United States Patent
Galarneau et al.

(10) Patent No.: US 11,308,783 B2
(45) Date of Patent: Apr. 19, 2022

(54) MEDICAL DEVICE FOR FALL DETECTION

(71) Applicant: Medtronic, Inc., Minneapolis, MN (US)

(72) Inventors: Michelle M. Galarneau, Minneapolis, MN (US); Brian B. Lee, Golden Valley, MN (US); Andrew Radtke, Minneapolis, MN (US); Vinod Sharma, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/879,499

(22) Filed: May 20, 2020

(65) Prior Publication Data

US 2020/0380840 A1    Dec. 3, 2020

Related U.S. Application Data

(60) Provisional application No. 62/854,086, filed on May 29, 2019.

(51) Int. Cl.
| | |
|---|---|
| *G08B 29/18* | (2006.01) |
| *G08B 21/04* | (2006.01) |
| *A61B 5/06* | (2006.01) |
| *A61B 5/11* | (2006.01) |
| *A61B 5/00* | (2006.01) |

(52) U.S. Cl.
CPC ............ *G08B 21/043* (2013.01); *A61B 5/067* (2013.01); *A61B 5/1116* (2013.01); *A61B 5/1117* (2013.01); *A61B 5/7264* (2013.01); *G08B 21/0446* (2013.01); *G08B 29/185* (2013.01)

(58) Field of Classification Search
CPC ..... A61B 5/1117; A61B 5/1116; A61B 5/002; A61B 5/7267; A61B 5/7264
See application file for complete search history.

(56) References Cited

U.S. PATENT DOCUMENTS

| | | | |
|---|---|---|---|
| 8,814,811 B2 | 8/2014 | Scholten et al. | |
| 10,198,928 B1 | 2/2019 | Ross et al. | |
| 2006/0282021 A1 | 12/2006 | DeVaul et al. | |
| 2013/0120147 A1* | 5/2013 | Narasimhan ..... | A61B 5/1117 340/573.1 |

(Continued)

OTHER PUBLICATIONS (PCT/US2020/034485) PCT Notification of Transmittal of the International Search Report and the Written Opinion of the International Searching Authority, dated Aug. 25, 2020, 11 pages.

(Continued)

*Primary Examiner* — Benyam Haile

(57) ABSTRACT

A medical device is configured to produce an accelerometer signal and detect a patient fall from the accelerometer signal. The device generates a body posture signal and a body acceleration signal from the accelerometer signal and detects a patient fall in response to determining that the body posture signal and the body acceleration signal meet fall detection criteria. The medical device is configured to receive a truth signal from another device that is not the medical device. The truth signal may indicate that the detected patient fall is a falsely detected patient fall and, responsive to receiving the truth signal, the medical device adjusts at least one fall detection control parameter.

23 Claims, 8 Drawing Sheets

(56) References Cited

U.S. PATENT DOCUMENTS

2013/0121147 A1   5/2013  Narasimhan et al.
2016/0038061 A1*  2/2016  Kechichian ........ G08B 21/0446
                                                600/301
2016/0328952 A1* 11/2016  Will ........................ H04M 3/46
2017/0055882 A1   3/2017  Al-Ali et al.
2019/0320945 A1* 10/2019  Johnson ................. G16H 50/20

OTHER PUBLICATIONS

Charlon, Yoann, et al., "Design and evaluation of a device worn for fall detection and localization: Applicaiton for the continuous monitoring of risks incurred by dependents in an Alzheimer's care", Expert Systems With Applications; Jul. 17, 2013; pp. 7316-7330; vol. 40: No. 18; Oxford, GB.

Abbate, Stefano, et al., "Monitoring of human movements for fall detection and activities recognition in elderly care using wireless sensor network: A survey", Retrived from Internet: URL:http://cdn.intechopen.com/pdfs-wm/12472.pdf, 23 pages, Dec. 14, 2010.

\* cited by examiner

MEDICAL DEVICE FOR FALL DETECTION

REFERENCE TO RELATED APPLICATION

This application claims the benefit of provisional U.S. Patent Application No. 62/854,086, filed on May 29, 2019, entitled "Medical Device for Fall Detection" and incorporated herein by reference in its entirety.

TECHNICAL FIELD

This disclosure relates to a medical device including an accelerometer for detecting that a patient has fallen.

BACKGROUND

A variety of medical devices are available or have been proposed for monitoring a patient and/or deliver a therapy. Such devices may be implantable, wearable, or external monitoring devices and may include or be coupled to one or more sensors for sensing a signal correlated to a condition of the patient. Some medical devices may detect an adverse condition from a sensor signal and deliver a therapy or generate an alarm to alert the patient or a caregiver. An accelerometer may be included in some medical devices, such as pacemakers, for determining patient physical activity, e.g., in order to provide cardiac pacing at a pacing rate according to the patient's level of activity. An accelerometer may also be used for determining a patient's posture.

Some patients, e.g., elderly or frail patients or patients experiencing a neurological or other medical condition, may be prone to falling down. Falls may result in injury. Complications due to fall-related injuries can arise and become more serious to the patient if left untreated. In some instances, falls may not result in injury, but may be an indication of worsening health. The cause of a fall may be related to an undiagnosed medical condition or a medical condition that has worsened.

SUMMARY

The techniques of this disclosure generally relate to a medical device system including an accelerometer producing a signal correlated to patient body posture and patient body acceleration. The medical device may be an implantable medical device (IMD) or a wearable device and is configured to detect a fall of a patient based on detecting a change in patient body posture and detecting an accelerometer signal spike corresponding to the impact of the fall in some examples. The medical device may set various thresholds for detecting a body posture change and an accelerometer signal spike corresponding to acceleration and/or impact during the fall. A fall may be detected when the change in body posture and the accelerometer signal spike both occur within a predetermined fall time window from each other. As disclosed herein, the medical device may adjust one or more fall detection control parameters to avoid false fall detection and to avoid undetected falls. The medical device may determine a metric of fall severity, which may be used for prioritizing data storage capturing the fall event relative to storage of other detected fall data.

In one example, a medical device includes an accelerometer configured to produce an accelerometer signal and a control circuit configured to generate a body posture signal and a body acceleration signal from the accelerometer signal, determine that the body posture signal and the body acceleration signal meet fall detection criteria, and detect a patient fall in response to the body posture signal and the body acceleration signal meeting the fall detection criteria. The medical device may also include a telemetry circuit configured to receive a truth signal from another device which may indicate that the detected patient fall is a falsely detected patient fall. Responsive to receiving the truth signal, the control circuit is further configured to adjust at least one fall detection control parameter used in detecting a patient fall. The adjusted fall detection control parameter may be used by the control circuit to control at least one of: generating the body posture signal from the accelerometer signal; generating the body acceleration signal from the accelerometer signal; or determining that the fall detection criteria are met.

In another example, a method for detecting a patient fall by a medical device includes producing an accelerometer signal and generating a body posture signal and a body acceleration signal from the accelerometer signal. The method further includes determining that the body posture signal and the body acceleration signal meet fall detection criteria, detecting a patient fall in response to the body posture signal and the body acceleration signal meeting the fall detection criteria. The method may further include receiving a truth signal from another device which may indicate that the detected patient fall is a falsely detected patient fall, and, responsive to receiving the truth signal, adjusting at least one fall detection control parameter. The fall detection control parameter may be used by the medical device to control generating the body posture signal from the accelerometer signal, generating the body acceleration signal from the accelerometer signal, or determining that the fall detection criteria are met.

In yet another example, a non-transitory computer readable medium stores instructions which, when executed by a control circuit of a medical device, cause the medical device to produce an accelerometer signal, generate a body posture signal and a body acceleration signal from the accelerometer signal and determine that the body posture signal and the body acceleration signal meet fall detection criteria. The instructions further cause the medical device to detect a patient fall in response to the body posture signal and the body acceleration signal meeting the fall detection criteria. The instructions may further cause the device to receive a truth signal from another device, which may indicate that the detected patient fall is a falsely detected patient fall. The instruction may cause the device to adjust at least one fall detection control parameter responsive to receiving the truth signal. The adjusted fall detection control parameter may be used by the medical device to control at least one of: generating the body posture signal from the accelerometer signal; generating the body acceleration signal from the accelerometer signal; or determining that the fall detection criteria are met.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

A medical device, which may be implantable or wearable, is configured to detect a patient fall based on a change in body posture and an accelerometer signal spike indicative of fall impact. According to the techniques disclosed herein, the medical device may automatically adjust criteria for fall detection in response to a truth signal indicating that a detected fall was a false fall detection and/or a fall that actually occurred was undetected by the medical device. The medical device may further determine a fall recovery time, e.g., based on a change in body posture subsequent to the fall detection, for selecting an appropriate fall detection response, which may include prioritizing data and information relating to detected falls that are stored in the medical device memory. The techniques disclosed herein may be implemented in a variety of medical devices, which may include neurostimulators, cardiac pacemakers or defibrillators, drug pumps, cardiac signal monitors, or other medical monitoring devices which may or may not include therapy delivery capabilities.

Figure 1:
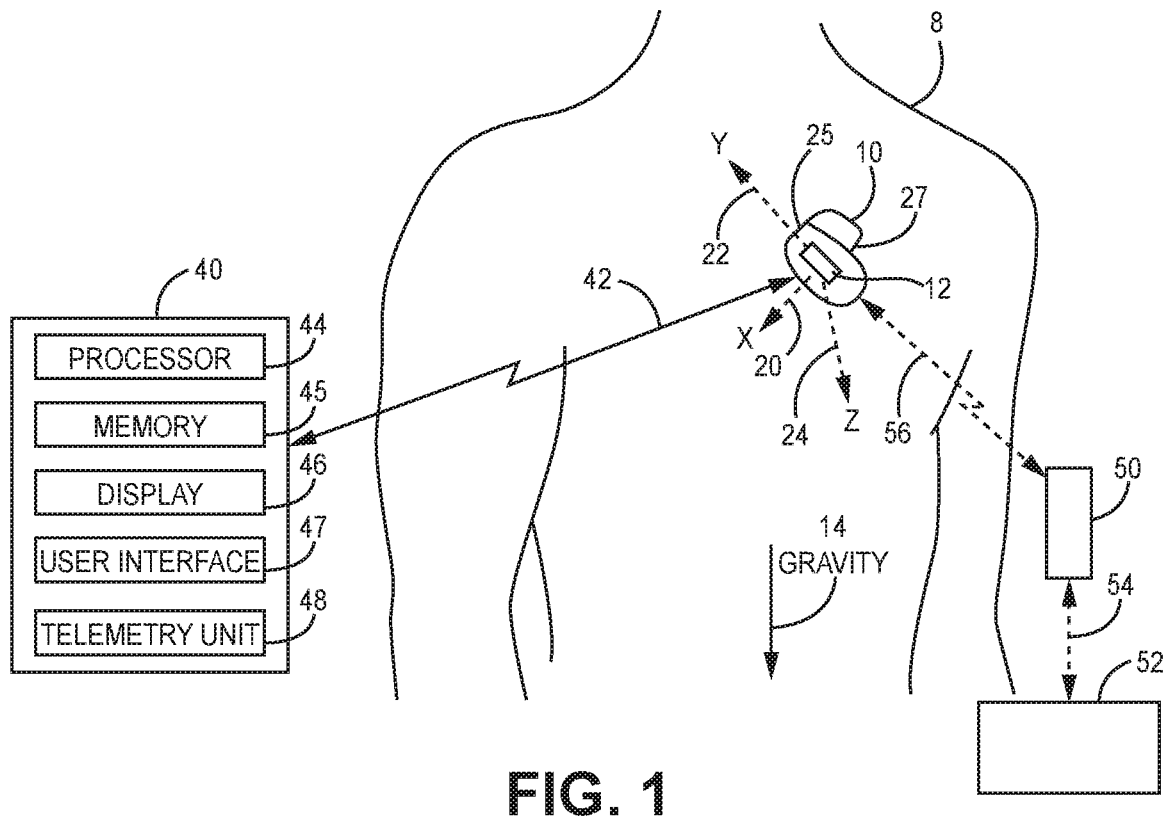
FIG. 1 is a schematic diagram of an IMD implanted in a patient and including an accelerometer for use in detecting if a patient has fallen.

FIG. 1 is a schematic diagram of an IMD 10 implanted in a patient 8 and including an accelerometer 12 for use in detecting if a patient has fallen. While examples described herein relate to an IMD, it is to be understood that the disclosed techniques may be implemented in a wearable medical device, which may be included in or on a watch, band, strap, belt or other wearable substrate. A medical device system performing the techniques disclosed herein at least includes an accelerometer producing a signal correlated to patient body posture with respect to gravitational force and patient body motion for use in detecting a patient fall. The medical device system may include additional sensors for monitoring other conditions or physiological signals of a patient, which may be used in some examples for corroborating fall detection based on the accelerometer signals.

As used herein, the terminology "has fallen" is distinguished from "is falling" in that if the patient "has fallen" the patient has already made impact with a surface such as the ground or floor. When a patient "is falling", the patient is still in the process of falling and has not yet made impact with a surface. In other words, the patient that "is falling" is still moving through the air and has not yet struck the ground or another surface; the patient that "has fallen" has made impact with a surface and is highly likely to be in a non-upright position subsequent to the impact, at least initially, e.g., until recovery from the fall occurs.

The term "body posture" as used herein refers to the position of a patient's body relative to earth's gravity. An "upright posture" as used herein generally refers to a body position in which at least the patient's upper body is relatively aligned with gravity. Examples of upright postures include, but are not limited to, standing, walking, running and sitting. A "non-upright posture" is typically a body position in which at least the patient's upper body is not relatively aligned with gravity. Examples of non-upright postures include, but are not limited to, prone, supine, reclining and side-lying positions. While a patient fall may commonly occur from an upright or vertical posture to a non-upright posture or horizontal posture, techniques disclosed herein include methods for detecting a fall from a non-upright posture or horizontal posture, e.g., when a patient rolls out of bed from a lying posture and lands on the floor in a non-upright posture.

IMD 10 includes a housing 25 that defines a hermetically sealed internal cavity in which internal components of IMD 10 reside. Housing 25 encloses circuitry that performs the functions of IMD 10 as attributed herein, including, for example, signal sensing circuitry, therapy delivery circuitry, a control circuit, memory, telemetry circuit, accelerometer 12, and a power source as generally described in conjunction with FIG. 3 below. The housing 25 may be formed from an electrically conductive material including titanium or titanium alloy, stainless steel, MP35N (a non-magnetic nickel-cobalt-chromium-molybdenum alloy), platinum alloy or other bio-compatible metal or metal alloy. In other examples, housing 25 is formed from a non-conductive material including ceramic, glass, sapphire, silicone, polyurethane, epoxy, acetyl co-polymer plastics, polyether ether ketone (PEEK), a liquid crystal polymer, or other biocompatible polymer.

In some examples, IMD 10 may be a leadless device that does not require medical leads extending away from housing 25. In other examples, a connector assembly 27, sometimes referred to as a "header," may be coupled to housing 25. Connector assembly 27 may have one or more connector bores for receiving a medical electrical lead and a required number of electrical feedthroughs for electrically coupling the medical electrical lead connector to circuitry enclosed within housing 25. For example, when IMD 10 is embodied as a pacemaker, implantable cardioverter defibrillator, or neurostimulator, IMD 10 may be coupled to one or more leads carrying electrodes that are deployed at an anatomical location away from the implant site of IMD 10. While leads are not shown in FIG. 1, it is to be understood that the fall detection techniques and hardware, firmware and/or software for performing the fall detection techniques disclosed herein may be implemented in a variety of IMDs that operate in conjunction with one or more medical leads as well as leadless IMDs that do not require leads to be coupled to the IMD.

IMD 10 includes accelerometer 12 that may be enclosed within housing 25 (or in some cases mounted along housing 25 or in connector block 27) or carried by a lead extending from IMD 10. Accelerometer 12 may be included in an accelerometer circuit 90 as described below in conjunction with FIG. 3, which may include one or more processing units that generate one or more accelerometer signals indicating acceleration. In some examples, the processing units of the accelerometer circuit may also be capable of processing or manipulating the one or more accelerometer signals and transmitting the processed (or unprocessed) signals to another component of IMD 10. Hence, accelerometer 12 may be included in an accelerometer circuit having the components for generating the accelerometer signals and/or the components for processing the accelerometer signals. In addition, while certain functions are described herein as being performed by the accelerometer circuit 90 shown in FIG. 3 or specifically the accelerometer 12 for conceptual purposes, it should be understood that such functions may additionally or instead be performed by another component of IMD 10, such as a control circuit 80 included in IMD 10 as described below in conjunction with FIG. 3 or a processor 44 of an external device 40 described below.

For example, accelerometer 12 may include a three-axis (three dimensional) accelerometer that produces a signal along each of three different accelerometer axes, labeled x-, y- and z-, by respective accelerometer elements. The x-, y- and z-signal components produced by each respective accelerometer element define a resultant output vector signal correlated to the patient's body posture relative to gravity. A change in the direction of the resultant output vector within a specified time interval, e.g., within a few seconds or less, indicates a change in the patient's posture, assuming the device orientation within the patient's body has not significantly changed over the same time period. The orientation of the three-axis accelerometer 12 with respect to gravity 14 when the patient 8 is in an upright posture may vary between patients and may vary over time since the implanted orientation of the IMD 10 with respect to gravity 14 may vary, e.g., with device shifting or rotation. However, relative changes in the direction of the resultant output vector of the three-dimensional accelerometer that occur with changes in the patient's body posture or orientation relative to gravity can be identified for use in detecting a patient fall.

In some examples, the three-axis accelerometer 12 includes three orthogonally arranged one-axis accelerometer elements each producing a respective signal component corresponding to acceleration in an x-direction 20, a y-direction 22, or a z-direction 24. In other examples, three single-axis accelerometer elements may be arranged in a non-orthogonal configuration wherein each accelerometer element is positioned along a unique plane relative to the other two accelerometers.

In the example shown, IMD 10 is a subcutaneous, leadless device, however in other examples one or more leads may extend from IMD 10 for positioning electrodes or other sensors, including accelerometer 12 in some examples, at a desired anatomical location away from the IMD housing 25. IMD 10 is shown implanted along a pectoral location but may be implanted in other subcutaneous or submuscular locations or sub-sternally, e.g., within the patient's thoracic cavity or intracardially within a heart chamber, or within another organ.

IMD 10 is configured to communicate with an external device 40 via a communication link 42. External device 40 may be referred to as a "programmer" used in a hospital, clinic or physician's office to retrieve data from IMD 10 and to program operating parameters and algorithms in IMD 10 for controlling IMD functions, including fall detection control parameters as well as other IMD sensing and/or therapy delivery functions. External device 40 may alternatively be embodied as a home monitor for retrieving data from IMD 10 for transmission to a centralized database or computer to enable remote monitoring of the patient 8 by a clinician. External device 40 may include a processor 44, memory 45, display unit 46, user interface 47 and telemetry unit 48. Processor 44 controls external device operations and processes data and signals received from IMD 10. Display unit 46, which may include a graphical user interface, displays data and other information to a user for reviewing IMD operation and programmed parameters and may display accelerometer signals retrieved from IMD 14 relating to fall detection.

User interface 47 may include a mouse, touch screen, key pad or the like to enable a user to interact with external device 40 to initiate a telemetry session with IMD 10 for retrieving data from and/or transmitting data to IMD 10, including programmable parameters for controlling fall detection as described herein. Telemetry unit 48 includes a transceiver and antenna configured for bidirectional communication with a telemetry circuit included in IMD 10 and is configured to operate in conjunction with processor 44 for sending and receiving data relating to IMD functions, which may include data relating to fall detection, via communication link 42.

Communication link 42 may be established between IMD 10 and external device 40 using a wireless radio frequency (RF) link such as BLUETOOTH®, Wi-Fi, or Medical Implant Communication Service (MICS) or other RF or communication frequency bandwidth or communication protocols. Data stored or acquired by IMD 10, including accelerometer signals or associated data derived therefrom, results of device diagnostics, and histories of detected falls and sensing and/or therapy delivery function of IMD 10, may be retrieved by external device 40 following an interrogation command. It is recognized that in some examples, IMD 10 may communicate with an external device via a relay device that may be another implantable medical device receiving signals from IMD 10 and transmitting signals on to external device 40. For example, when IMD 10 is implanted within the abdominal cavity or thoracic cavity, which may be outside or within the heart or another organ, IMD 10 may communicate with another implantable medical device via RF communication, tissue conductance communication or other implemented communication protocol for relaying data to external device 40.

IMD 10 is further shown in communication with a personal communication device 50, which may be a smart phone, tablet or other device used by the patient and configured to communicate with IMD 10 via communication link 56, e.g., via a BLUETOOTH® link. Personal communication device 50 may be configured to pair with another device or appliance 52 via BLUETOOTH® (or other) communication link 54 as the patient goes about their daily activities. For example, appliance 52 may be a weighing scale, an automobile audio system, a computer mouse or keyboard, a fitness tracker, etc. As described herein, IMD 10 may receive wireless signals via link 56 from a patient's external personal device 50 that indicate a patient activity, which may involve the appliance 52 that communicates with the personal device 50. The indicated patient activity, such as standing on a weighing scale, driving or sitting in a car, sitting at a computer, or walking or jogging, may be used by IMD 10 to facilitate determination of or confirm a reference upright body posture.

Figure 2:
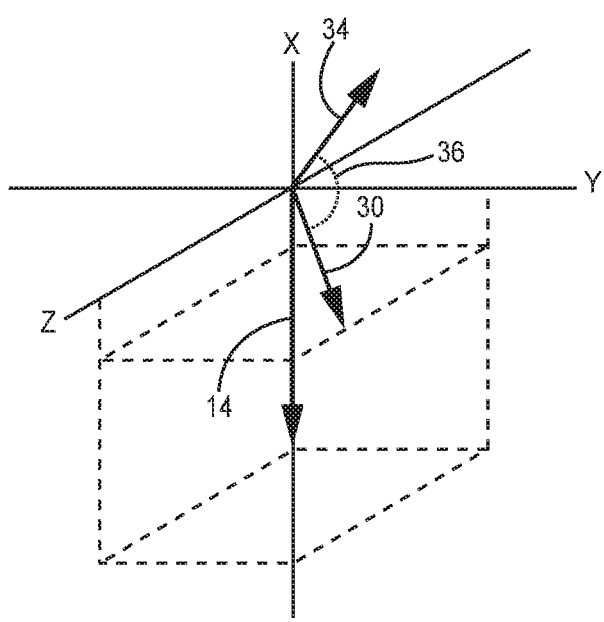
FIG. 2 is a conceptual diagram of three-dimensional output vectors of a three-axis accelerometer with respect to gravity.

FIG. 2 is a conceptual diagram of resultant output vectors 30 and 34 of a three-axis accelerometer with respect to gravity 14. In order to detect a fall, an acceleration signal spike is detected from a high pass or band pass filtered accelerometer signal correlated to patient body motion. Additionally, a change in patient body posture is detected from a low pass filtered accelerometer signal correlated to changes in the patient's body position relative to gravity 14. The acceleration signal spike detected from the band pass filtered accelerometer signal and the change in patient body posture detected from the low pass filtered accelerometer signal may be required to fall within a time window from each other in order to meet fall detection criteria. When a fall occurs, a change in body posture and an acceleration signal spike are contemporaneous.

In one example, an output vector 30 shown in FIG. 2 may represent a resultant body acceleration signal vector at a sampling time of the body acceleration signal acquired by bandpass filtering the output signal of each of the x-, y- and z-axis accelerometer elements. The magnitude of the resultant output vector 30 may be computed as a mathematical combination of the x, y and z components of the accelerometer signal. In some examples, the magnitude of output vector 30 is computed as a Euclidean norm, i.e., the square root of the sum of squares of the three orthogonal x-, y- and z-component vectors:

$$\|v\|=(x^2+y^2+z^2)^{1/2}$$

In general, the magnitude of the output vector is 1.0 g (9.8 m/s$^2$) if there is no acceleration/deceleration of the three-axis accelerometer. Upon impact with the ground or other surface due to a patient fall, the magnitude of the output vector 30 is expected to exceed a threshold magnitude. In other examples, the magnitude of an output acceleration vector at a given sample time may be determined by summing the amplitudes of the three acceleration signal components at the sample time.

As described herein, the magnitude, slew rate, and/or frequency of the body acceleration signal may be determined for detecting an acceleration signal spike in the bandpass (or high pass) filtered accelerometer signal. The high magnitude and high frequency spike may be correlated to a fall, particularly upon reaching a maximum acceleration during the fall and striking the floor or ground upon impact. The magnitude of the body acceleration signal may be determined at a regular sampling interval or in response to a triggering event, e.g., a detected change in body posture, for determining if the magnitude meets a spike detection threshold magnitude. In some examples, in addition to or instead of determining if a magnitude of the accelerometer signal reaches a threshold magnitude, an acceleration signal spike corresponding to a patient fall may be detected by detecting a positive slew rate of the accelerometer signal meeting a positive slew rate threshold. In some examples, the acceleration signal spike detection may require detecting the positive slew rate followed by a negative slew rate both meeting a respective positive and negative slew rate threshold with both slew rates occurring within a specified time interval of each other such that the slew rates correspond to a single signal spike. In this way, a high frequency body acceleration signal corresponding to a fall may be detected in the time domain.

In order to capture an acceleration signal spike caused by a fall, the three-dimensional (or a two-dimensional or single axis) accelerometer signal may be bandpass filtered to remove DC components and high frequency noise. The accelerometer signal may be filtered by a 1 to 30 Hz bandpass filter or a 1 to 10 Hz bandpass filter, as examples, to obtain an output signal that includes acceleration caused by body motion during a fall and upon impact. The filter may be an adjustable filter having cutoff frequencies set tailored to an individual patient to optimize fall detection performance, e.g., to reduce a false fall detection rate and/or reduce the likelihood of undetected falls. For example, IMD 10 may monitor the accelerometer signal over a period of time (e.g., one day, one week or more) to determine the frequency range of the accelerometer signal during the patient's normal daily physical activity, e.g., associated with activities of daily living (ADL). The frequency range of the patient's ADL may be used by the control circuit or processing circuitry of IMD 10 to determine and set the high pass and/or low pass cutoff frequencies of the band pass filter used to generate a body acceleration signal from the signal produced by accelerometer 12. An acceleration signal spike may be detected from the body acceleration signal for detecting a patient fall.

The output signals of a three-dimensional accelerometer may be also be used to determine a change in body posture or position relative to gravity. In this case, a low pass filtered signal from each accelerometer axis is acquired to acquire a body posture signal. The accelerometer signal from each axis may be filtered by a 1 Hz low pass filter as an example, with higher frequency acceleration signals due to body motion removed.

In the example shown in FIG. 2, the two output vectors 30 and 34 may be obtained from low pass filtered signals (instead of vector 30 being obtained from a bandpass filtered body acceleration signal as described in the preceding example). In this case, these two body posture vectors 30 and 34 are determined at two different time points, e.g., ranging from two to twelve seconds apart, for detecting a change in body posture relative to gravity 14. The angle 36 between output vector 30 and output vector 34 represents the change in direction from body posture vector 30 to body posture vector 34 from one time point corresponding to vector 30 to another time point corresponding to vector 34. The angle 36 may be determined by using the inverse cosine of the dot product of the two output vectors 30 and 34 divided by the product of their magnitudes. In some examples, to simplify computations, the dot product of the two vectors 30 and 34 may be determined and the resulting scalar may be used as a metric of the angle 36 between the two output vectors. The angle 36, the scalar result of the dot product, or another metric of the directional change between two body posture vectors obtained from a low pass filtered accelerometer signal is correlated to a change in patient body posture relative to gravity 14. The metric of the directional change between two body posture vectors obtained at two different time points may be compared to a change threshold to determine if the metric meets fall detection criteria.

Figure 3:
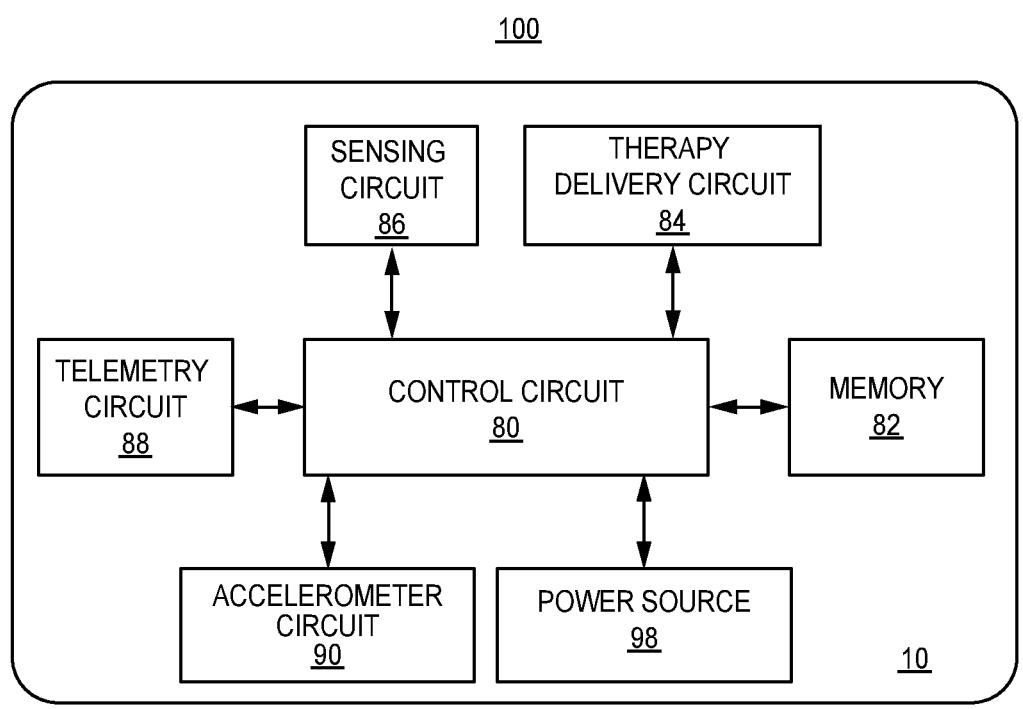
FIG. 3 is a block diagram of circuitry that may be enclosed within the housing of the IMD of FIG. 1 to provide fall detection according to one example.

FIG. 3 is a block diagram 100 of circuitry that may be enclosed within housing 25 of IMD 10 to provide the functions disclosed herein for performing fall detection according to one example. IMD 10 may include control circuit 80, memory 82, therapy delivery circuit 84, sensing circuit 86, telemetry circuit 88, accelerometer circuit 90 and power source 98. In some examples, IMD 10 is capable of delivering a therapy, which may be an electrical stimulation therapy such as a cardiac pacing therapy, cardioversion/defibrillation shock, neurostimulation, or muscle stimulation. In this case, therapy delivery circuit 84 may be coupled to electrodes, which may be carried on housing 25 and/or by medical electrical leads extending away from housing 25. In other examples, therapy delivery circuit 84 may be a drug pump for delivering a pharmaceutical or biological agent, such as an insulin pump. In this case, therapy delivery circuit may include a reservoir and port or catheter coupled thereto for retaining and delivering a fluid agent.

IMD 10 may include a sensing circuit for sensing mechanical, electrical, optical or chemical signals correlated to a physiological condition of the patient. For example, electrodes may be coupled to sensing circuit for sensing cardiac electrical signals or electrical nerve or muscle signals. IMD 10 may include a variety of sensors used in medical devices for monitoring a patient or detecting a physiological or pathological condition such as a pressure sensor, acoustical sensor, temperature sensor, impedance sensor, oxygen sensor, blood perfusion sensor, blood flow sensor, etc.

Control circuit 80 may receive signals from sensing circuit 86 and accelerometer circuit 90 for detecting a physiological condition and for use in controlling a therapy delivered by therapy delivery circuit 84. Control circuit 80 may include a processor configured to execute various monitoring and therapy delivery protocols stored in memory 82 and controls sensing circuit 86 and therapy delivery circuit 84 accordingly. Power source 98 may include one or more rechargeable or non-rechargeable batteries and provides power to control circuit 80 and each of the other circuits 82, 84, 86, 88 and accelerometer circuit 90 as needed.

Accelerometer circuit 90 includes accelerometer 12 which may be enclosed by housing 25 of IMD 10. However, it is recognized that when IMD 10 is coupled to one or more medical electrical leads, accelerometer 12 may be carried by the lead, e.g., along a distal portion of the lead, and coupled to circuit 90 within housing 25 via an electrical conductor. Accelerometer 12 (shown in FIG. 1) may include a one-, two- or three-axis accelerometer as described above. Each axis of accelerometer 12 may be defined by a piezoelectric element, micro-electrical mechanical system (MEMS) device or other sensor element capable of producing an electrical signal in response to changes in acceleration imparted on IMD 10 and subsequently the sensor element, e.g., by converting the acceleration to a force or displacement of the accelerometer sensor element that is converted to the electrical signal by the accelerometer sensor element.

Each accelerometer sensor element produces an acceleration signal corresponding to a vector component aligned with the axis of the sensor element. Each accelerometer sensor element produces a DC component corresponding to the vector component of gravitational force or other force exerted on the patient along the respective accelerometer axis. Each accelerometer sensor element produces an AC component correlated to the acceleration vector component due to motion of the patient, along the respective axis. Accelerometer circuit 90 may include a low pass filter with a relatively low cut off frequency, e.g., less than 2 Hz or 1 Hz or less, for generating a patient body posture signal that is correlated to the patient's body position relative to gravitational force. Accelerometer circuit 90 may further include a bandpass filter having a bandpass from 1 to 30 Hz, 1 Hz to 20 Hz, or 1 to 10 Hz as examples for generating a body acceleration signal. The bandpass filtered body acceleration signal is correlated to acceleration due to patient body motion, e.g., during patient physical activity and during a fall and fall impact. Each of the low pass filtered body posture signal and the bandpass filtered body acceleration signal are received by control circuit 80 for detecting a patient fall as disclosed herein. Accelerometer circuit 90 may include one or more analog-to-digital converters (ADCs) for providing multi-bit digital signals to control circuit 80 for analysis and processing for detecting a patient fall.

A bandpass filtered patient physical activity signal may also be generated by accelerometer circuit 90 that is used by control circuit 80 to determine a metric of physical activity of the patient. The bandpass filtered cutoff frequencies for generating a patient physical activity signal may be different than the bandpass filtered cutoff frequencies for generating a body acceleration signal used for detecting an acceleration signal spike for fall detection. The patient physical activity metric may be determined to corroborate fall detection criteria based on a directional change in a body posture vector determined from the low pass filtered body posture signal and a high magnitude and/or high slope or frequency body acceleration signal. For example, a low, non-changing level of the patient physical activity metric after a detected acceleration signal spike supports a positive detection whereas a relatively high patient activity metric may indicate that the patient is engaged in physical activity and that the fall detection is false.

The patient physical activity metric(s) and/or a snippet of the patient activity signal just prior to fall detection may be included in fall detection data stored in memory 82, e.g., along with raw accelerometer signals, the generated body posture signal and/or generated body acceleration signal, to provide useful information in understanding what the patient was doing prior to or what may have caused the fall. The patient activity metric(s) and/or a snippet of the patient activity signal after the fall detection may be stored in memory 82 with fall detection data. In some cases, patient physical activity after a fall may be an indication of a false fall detection or fall recovery, but in other cases patient physical activity may be due to seizure or reaction to pain. The storage of patient activity signal following a fall detection may be used in verifying future fall detections, e.g., based on an analysis of the post-fall patient activity signal morphology as described below in conjunction with FIG. 4.

Control circuit 80 may determine the patient physical activity metric from the accelerometer signal at a desired frequency for use in determining a sensor-indicated pacing rate (SIR) when IMD 10 is embodied as a pacemaker, for example. The physical activity metric may vary between a minimum resting level and a maximum activity level associated with maximum exertion. In some examples, the activity metric is determined as an activity count. Control circuit 80 may include a counter to track the activity count as the number of times the patient physical activity signal from accelerometer circuit 90 crosses a threshold during an activity count interval, for example a 2-second interval. The count at the end of each activity count interval is correlated to patient body motion during the activity count interval and is therefore correlated to patient physical activity. The threshold applied to the accelerometer signal, which when crossed by the motion sensor signal causes the activity count to be increased, may be a default or programmable threshold or may be an automatically adjusted threshold. Example methods for obtaining an activity count over an n-second interval are generally disclosed in U.S. Pat. No. 5,720,769 (van Oort), incorporated herein by reference in its entirety.

In other examples, an activity metric may be obtained from the accelerometer signal by integrating or summing motion signal sample points over an activity count interval, e.g., a two-second interval though longer or shorter intervals of time may be used for determining an activity metric. The activity metric may be used to identify the ADL range, corresponding to normal daily activities, such as moving about the home, driving a car, light tasks, etc. Other example methods for determining a patient physical activity metric are generally disclosed in U.S. Pat. No. 6,449,508 (Sheldon, et al.), incorporated herein by reference in its entirety.

Other types of sensors may be included in sensing circuit 86 which may produce a signal correlated to patient physical activity or other patient physiological conditions. Such sensors include sensors of heart rate, respiratory activity, such as minute ventilation, or blood or tissue oxygen saturation. Other types of sensors may be used for providing control circuit 80 with a signal correlated to physical activity of the patient or other physiological condition for use in confirming a detected fall or provide pre- or post-fall data or information that is stored with detected fall data for transmission to external device 40 for review by a clinician.

Control circuit 80 may receive a body acceleration signal, a body posture signal, and a patient physical activity signal from accelerometer circuit 90. Each of these signals may include one or more single axis signal components and/or any combination of two or all three axis signal components. Each signal is filtered over a bandwidth that includes the signal content relating to fall acceleration, body posture changes relative to gravity, and patient physical activity, respectively, as described above. Control circuit 80 may include processing circuitry for sampling, averaging and analyzing each of the body acceleration signal, the body posture signal and in some examples the patient physical activity signal generated by accelerometer circuit 90 for fall detection according to the techniques disclosed herein.

Control circuit 80 performs a response to a fall detection which may include storing fall related data in memory 82, generating an alert or notification (which may be transmitted by telemetry circuit 88), adjusting sensing performed by sensing circuit 86 for monitoring other physiological signals of the patient, and/or adjusting a therapy delivered by therapy delivery circuit (which may include turning on or off a therapy).

Telemetry circuit 88 may include a transceiver and antenna for communicating with external device 40 via communication link 42 as described above in conjunction with FIG. 1. Telemetry circuit 88 may further include a transmitter and receiver for communicating with a personal device 50 via link 56, e.g., via Wi-Fi or BLUETOOTH®, as described above. Communication with personal device 50 may be performed to facilitate detection and validation of patient body posture based on the patient body posture signal and information received from personal device 50. As described below, control circuit 80 may control telemetry circuit 88 to transmit a query or ping to external device 40 or personal device 50 to request confirmation or a log of data relating to times that the patient is highly likely to be in an upright position and for transmitting notifications or alerts to external device 40 or personal device 50 relating to detected patient falls. Telemetry circuit 88 may receive "truth" data from external device 40 and/or personal device 50 for confirming fall detections and, in some instances, learning of a missed fall detection. Control circuit 80 may use truth data for adjusting fall detection control parameters and methods used in fall detection to increase sensitivity and/or specificity of the fall detection techniques.

Figure 4:
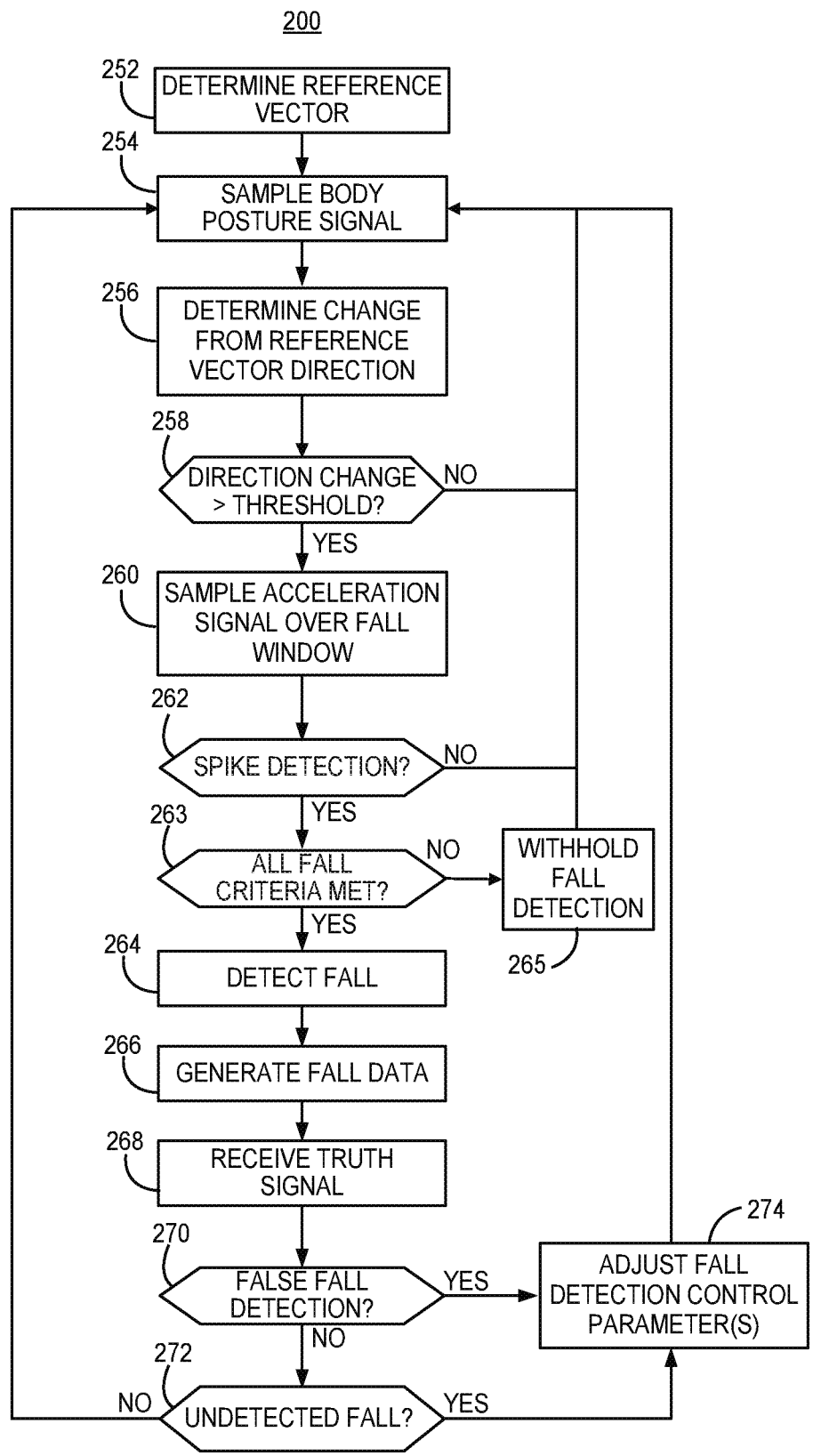
FIG. 4 is a flow chart of a method performed by a medical device for detecting a patient fall according to one example.

FIG. 4 is a flow chart 200 of a method performed by IMD 10 for detecting a patient fall according to one example. At block 252, control circuit 80 determines a reference vector from the body posture signal. At block 254, control circuit 80 samples the body posture signal to obtain a current body posture signal vector. The current body posture vector and the reference vector are analyzed for detecting a directional change from the reference vector to the current body posture vector that meets fall detection criteria. A change in direction of the body posture vector is correlated to a change in the patient's body posture relative to gravity. In some examples, the reference vector determined at block 252 is the body posture vector that corresponds to an upright body posture and is established based on the body posture signal acquired at a time that the patient is verified to be in an upright position, e.g., as instructed during an office visit or based on a signal from external device 40 or personal device 50 that indicates an upright posture. In some examples, control circuit 80 may verify that other requirements are met for establishing a reference vector from a stable, reliable body posture signal. Such requirements may include verifying that the patient physical activity is low based on a physical activity signal generated from the accelerometer signal (e.g., a patient physical activity metric is below a predetermined threshold level) and/or verifying that the reference vector magnitude is about 1 g due to gravitational force acting on the patient in the absence of other acceleration forces acting on the patient. The upright reference vector may be stored in memory 82 and retrieved from memory 82 for comparison to a currently sampled body posture vector. Examples of techniques for establishing an upright or vertical reference vector at block 252 are described below in conjunction with FIG. 5 through 7.

In other examples, the reference vector determined at block 252 is a body posture vector that is sampled from the low pass filtered accelerometer signal at a previous time point than the sampled body posture vector obtained at block 254. By determining the reference vector at a preceding time point, control circuit 80 is enabled to detect a relative change in direction of the body posture vector from the preceding time point to the current time point. The reference vector determined at block 252 may be the body posture vector determined five to ten seconds earlier, e.g., six seconds earlier, than a currently sampled body posture vector obtained at block 254.

At block 254, control circuit 80 samples the body posture signal received from accelerometer circuit 90 for detecting a change in patient body posture according to a fall detection protocol. For example, the body posture signal may be sampled selected hours of the day (or night) or continuously at a desired sampling rate. The sampling may include sampling the body posture signal at a desired sampling rate then averaging sampled signals over a predetermined averaging time interval to obtain an average body posture vector. In one example, the body posture signal is sampled at 32 Hz or lower, and the sampled signals acquired over a one to two second time interval are averaged to obtain the average body posture vector for the n-second interval. When a three dimensional accelerometer signal is received, each of the sampled x-, y- and z-components of the body posture signal may be averaged over the predetermined time interval to obtain average x-axis, y-axis and z-axis components of the body posture signal. The averaged body posture vector at the n-second time point may then be determined as the currently sampled body posture vector defined by the averaged x-, y- and z-components. When the averaging time interval is two seconds, the reference vector may be the average body posture vector obtained six seconds earlier than the current body posture vector, in one example.

At block 256, a metric of the directional change between the reference vector and the current body posture vector is determined. As discussed in conjunction with FIG. 2, a directional change metric may be computed as an angle between the reference vector and current body posture vector by determining the inverse cosine of the dot product of the current body posture vector and the reference vector divided by the product of their magnitudes. This angle is correlated to the change in the patient's body position relative to gravity. Alternatively, the scalar result of the dot product of the reference vector and the current body posture vector may be determined as a directional change metric that is correlated to the angle between the reference vector and the body posture vector. In other examples, other methods may be used for determining a metric correlated to the change in direction (or angle) between the current body posture vector and the previously determined reference vector, e.g., by determining and analyzing differences between the respective x-, y- and z-vector components. Another method for determining a metric of the directional change of the body posture signal is described below in conjunction with FIG. 10.

The determined angle or other directional change metric between the current body posture vector and the reference signal is compared to a fall detection threshold at block 258. It is expected that when a patient falls, the body posture vector direction will change by a threshold amount, e.g., corresponding to a change from an upright to a non-upright posture, within a predetermined time interval, e.g., within two seconds or less, within four seconds or less, or within six seconds or less. The threshold change may be an angle of at least 45 degrees, at least 50 degrees, at least 60 degrees or other predetermined threshold. In one example, if the angle between the current body posture vector and the reference vector is at least 57 degrees, control circuit 80 may determine that the body posture vector directional change meets fall detection criteria. When the scalar result of the dot product divided by the vector magnitudes of the current body posture vector and reference vector is used as the directional change metric the threshold may be set equal to the cosine of the corresponding threshold angle, e.g., cosine of 57 degrees or approximately 0.54. In some examples, the product of the vector magnitudes may be assumed to be 1 g eliminating the division step.

The fall detection criteria for detecting a change in body posture vector direction are not limited, however, to detecting a threshold change from an upright or vertical body position. Some patients may fall out bed in which case the body posture vector direction may change due to rolling of the patient during the fall from a substantially horizontal position on the bed to the floor. In some cases the patient may land in a substantially horizontal position but may land in a non- or semi-horizontal position, e.g., ending in a substantially seated position on the floor. In some cases, therefore, the reference vector may be the body posture vector four to six seconds earlier than the current body posture vector and the directional change between the reference vector and the current body posture vector corresponds to a rolling of the patient.

Using the example axis orientation shown in FIG. 2, where a longitudinal axis is the x-axis of the accelerometer 12, aligned substantially vertically with the direction of gravity when the patient is standing upright, the two radial axes, e.g., the y- and z-axes, may contribute the greatest change in direction as the patient rolls out of bed. Accordingly, determining the directional change from the reference vector may include analyzing the change in each vector component (each accelerometer axis signal) over a time period of one to six seconds, as an example, or analyzing the directional change of the resultant vector of the three vector components to determine whether a threshold directional change is reached, which may correspond to a rolling motion or rotation of the patient. A threshold directional change from a reference vector that is determined at a predetermined time interval earlier than the current body posture vector may be detected without requiring or verifying that the reference vector corresponds to an upright patient posture. In some examples, the current body posture vector may be compared to both an upright reference vector previously established when the patient is in a known upright position and to a previous body posture vector determined four to six seconds earlier, for example, than the current body posture vector.

When the change in body posture vector direction does not meet the fall detection criteria at block 258, control circuit 80 continues to sample the body posture signal at block 254. In some examples, the current body posture signal becomes the reference vector for a future comparison to a body posture vector for detecting a change in body posture vector direction that is greater than the change threshold and occurs within a predetermined time interval, which may be a multiple of the body posture signal averaging time interval. As such, the current body posture vector (i) may be stored in memory 82 as the reference vector for the i+3 body posture vector, determined six seconds later, as an example, when a new body posture vector is determined every two seconds. The current body posture vector (i) may be stored as the reference vector to be compared to the i+1 body posture vector, the i+2 body posture vector and/or i+n body posture vector in other examples.

When the directional change of the current body posture vector relative to the reference vector meets the fall detection requirement at block 258, control circuit 80 samples the bandpass filtered body acceleration signal received from accelerometer circuit 90 (block 260). The body acceleration signal may be sampled at a relatively higher frequency than the sampling rate of the body posture signal to enable detection of a relatively high frequency acceleration spike that occurs with a fall. The body acceleration signal may be sampled over a fall window that is a time window encompassing the body posture change detected at block 258 during which a possible fall associated with the body posture change may be detected. For example, the body acceleration signal may be buffered in memory 82 and, in response to a directional change of the body posture vector, the body acceleration signal may be sampled at a rate between 64 Hz and 256 Hz for up to 10 seconds before and 5 seconds after the body posture change detected at block 258. The body acceleration signal may be sampled at 128 Hz over a fall window extending four seconds earlier and one second after the time of the body posture vector that resulted in a threshold directional change detection at block 258.

In some examples, a single axis body acceleration signal is sampled and compared to a spike detection criteria at block 262. A single axis may be sensitive enough for detecting a high magnitude spike caused by a fall, and sampling a single axis may reduce power source current drain. For instance, the single axis signal sampled for spike detection during a fall window may be an accelerometer axis that is a radial axis or minor axis that may be subjected to less variation due the patient's ADL and to IMD rotation or orientation changes. However, when a single axis is being used, the optimal axis selected may vary between devices, implant position, patients, and over time since the axis that results in the most reliable spike detection due to a patient fall may vary with these and other factors.

In other examples, two or all three axis signals may be sampled for detecting a magnitude of the body acceleration signal that is equal to or greater than the magnitude threshold at block 262. A combination of the x-, y- and/or z-axis components may be selected as the body acceleration signal. The combination of axis signal components may be configured in hardware rather than a software or firmware processing function for determining the combination of axis signal components to conserve power source 98. The magnitude of the body acceleration signal may be determined as the magnitude of a sample point of a single axis, the sum of the absolute magnitude of concurrent sample points of two or all three axis signals, or the sum of the square of concurrent sample point magnitudes from two or all three axis signals.

At block 262, control circuit 80 may detect a body acceleration signal spike based on a threshold magnitude and/or threshold slew rate or other spike morphology criteria. As mentioned previously, a positive slew rate meeting a positive slew rate threshold followed by a negative slew rate meeting a negative slew rate threshold within a time limit following the positive slew rate may be required for detection of a body acceleration signal spike. An absolute value of the body acceleration signal may be compared to a magnitude threshold at block 262, e.g., by rectifying the ADC signal output of the bandpass filtered accelerometer signal and passing the rectified signal to a comparator. If the body acceleration signal does not meet the magnitude threshold and/or one or more slew rate thresholds during the fall window, a fall is not detected. Control circuit 80 continues to sample the body posture signal for detecting a posture change meeting fall detection criteria. Both a threshold change in body posture and a body acceleration signal spike are required to be detected within a predetermined time interval of each other, referred to herein as the "fall window" or "fall time window," in order to detect a fall in some examples.

When a body acceleration signal spike is detected at block 262 within the fall window encompassing the detected change in body posture, IMD 10 may detect a patient fall at block 264. In some examples, control circuit 80 may verify that other fall detection criteria are satisfied at block 263, prior to making the fall detection at block 264. For instance, control circuit 80 may analyze the body acceleration signal to verify that the detected spike is not one of multiple spikes occurring at a regular rhythm associated with a physical activity. Control circuit 80 may compare the magnitude and/or slew rate over the entire fall window or an extended physical activity analysis window that encompasses the fall window for detecting multiple spikes that may indicate a repetitive activity being performed by the patient. When multiple body acceleration signal spikes occur within the fall window or an extended time period encompassing the fall window, control circuit 80 may not detect a fall (e.g., withhold a fall detection based on the directional change and spike detection within a fall window). In some examples, control circuit 80 may determine whether multiple spikes exceeding the magnitude threshold are occurring at regular intervals suggesting a repetitive physical activity involving body posture changes and impact. When multiple spikes occur in cadence, e.g., over a time window longer than the fall window, control circuit 80 may determine that the body acceleration magnitude criteria are not met at block 262 and withhold fall detection at block 265. However, when at least one or multiple body acceleration signal spikes occur within the fall window meeting spike detection criteria a fall may be detected at block 264 when other patient body posture change criteria are also met. During some falls, such as down a staircase, multiple spikes may occur within a fall window and accompany a threshold body posture change.

It is recognized that other sensor signals may be used in corroborating a fall detection at block 263 such as blood pressure, cardiac electrical signal, patient physical activity (e.g., remaining low after the fall), or other signals produced by sensing circuit 86 and monitored by IMD 10. Such signals may be monitored for detecting other patient conditions or may depend on a medical condition that makes the patient prone to falling and provide a clinician with diagnostic or prognostic data for selecting and managing therapy for the patient. In some examples, control circuit 80 determines the patient physical activity metric at block 263 to verify that patient physical activity is low or below a threshold after the body acceleration signal spike and body posture change are detected. When other fall detection criteria are unmet, such as if post-spike physical activity is high, the fall detection based on the body posture change and the detected acceleration signal spike may be withheld at block 265. In some examples, when a fall detection is withheld at block 265 (fall not detected), control circuit 80 may generate and store data relating to the withheld fall detection. For example, an episode of the patient activity signal or other corroborating signals that caused the fall detection to be withheld (even though the directional change and spike were detected within a fall window) may be stored in memory 82, along with signals and/or data relating to the detected acceleration signal spike and the body posture change.

When all fall detection criteria are met, control circuit 80 detects the fall at block 264. At block 266, control circuit 80 generates fall data for storage in memory 82 and/or immediate or future transmission via telemetry circuit 88. In some examples, generating fall data at block 266 includes generation of a notification that may be transmitted to external device 40 and/or to the personal device 50 to notify a caregiver, clinician or first responder of the detected fall. For example, the notification may be transmitted to the personal device 50, and personal device 50 may be configured to send a text message, phone call or other form of messaging to a caregiver, first responder, or medical center.

The fall data generated at block 266 may include a time and date stamp and other sensor signal data that is acquired by sensing circuit 86 and/or any therapy being delivered by therapy delivery circuit 84. For example, when IMD 10 is configured to receive cardiac electrical signals, a cardiac electrical signal episode preceding and/or encompassing the detected fall may be stored with the fall data. In some examples, control circuit 80 continues to monitor the body posture signal after fall detection to determine a recovery time between fall detection and a subsequent body posture change (e.g., sitting up or standing up after the detected fall). The recovery time may be included in the fall data generated at block 266. As described in conjunction with FIG. 8, recovery time may be determined for use in prioritizing storage of fall data in memory 82 and/or generating a notification transmitted to an external device 40 or personal device 50.

IMD 10 may be configured to receive a truth signal at block 268 from another device, e.g., from external device 40 or personal device 50. In some examples, the truth signal may be a signal transmitted from an external device in response to the patient or a caregiver initiating the transmission following the detected fall. The truth signal may be transmitted in response to a prompt received from IMD 10 with the fall detection notification, requesting verification of the fall. In other examples, a list of detected falls with dates and time and other fall data may be generated by external device 40 or personal device 50 based on fall data received from IMD 10. The patient or a caregiver may select fall detections that correspond to actual falls to confirm true fall detections and confirmation signal data may be transmitted back to IMD 10. Fall detections that are not confirmed by the truth signal are flagged as false fall detections by IMD 10.

When a detected fall is identified as a false fall detection at block 270, control circuit 80 may adjust one or more fall detection control parameters at block 274. Control circuit 80 may determine if a threshold number or frequency of false fall detections has been reached before adjusting one or more fall detection control parameters. As examples, a magnitude threshold, slew rate threshold or other spike detection threshold, a directional change threshold, body posture signal averaging time interval, sampling rate, filtering cut off frequency, fall window starting and/or ending times relative to a detected acceleration signal spike or relative to a detected body posture change, or any combination thereof may be adjusted at block 274. In some examples, the adjustment at block 274 may include updating a reference vector corresponding to a known upright posture of the patient. In one example, a fall detection identified as a false fall detection based on a truth signal received at block 268 may cause control circuit 80 to increase the directional change threshold and/or increase the magnitude threshold, slew rate threshold, frequency threshold or other threshold used for detecting an acceleration signal spike.

The fall detection control parameter(s) may be adjusted at block 274 to increase specificity of fall detection by improving discrimination between posture and acceleration signals corresponding to a fall from posture and acceleration signals that occur when the patient has not fallen and may be engaging in other activities, such as exercise or sports that may involve sudden posture changes and/or high acceleration signal magnitudes. As described below in conjunction with FIG. 9, adjustment of the directional change threshold and/or acceleration magnitude threshold for spike detection may include an analysis of body posture vector direction changes and/or body acceleration signals, respectively, acquired over periods of activities of daily living and/or increased activity corresponding to exercise or other patient activity in order to establish ranges or trends of acceleration signals and body posture changes that occur during activities that the patient normally engages in that do not include a fall.

In examples that require other fall criteria at block 263 to be met based on corroborating signals, such as the patient physical activity or other sensed signals, adjustment of fall detection control parameters at block 274 may include an adjustment of other corroborating fall detection criteria. For example, if patient physical activity level is used to verify a fall detection based on body posture change and acceleration signal spike, the patient activity signal may cause a fall detection to be withheld due to post-fall activity being greater than a low activity threshold. However, if the withheld fall detection is subsequently confirmed to be a true fall based on a truth signal received at block 268, the post-fall patient physical activity threshold used to withhold a detected fall may be adjusted.

In other examples, when data and signals relating to the withheld fall detection are stored in memory 82, the morphology of the patient physical activity signal that caused a fall detection to be withheld may be analyzed so that patient physical activity morphology features may be used to match post-fall patient activity signal morphology for confirming a future fall detection. Such adjustments to post-fall physical activity signal morphology criteria may be useful in confirming falls relating to epileptic seizures, for example, in which morphology of the physical activity signal post-fall may correspond to seizure activity and should not cause a fall detection to be withheld.

When the truth signal does not include an indication of a false fall detection at block 270, fall detection control parameters may remain unadjusted, and control circuit 80 may return to monitoring the body posture signal and body acceleration signal for fall detection. While the truth signal is shown to be received after a fall detection, it is contemplated that a truth signal may be received after multiple falls have been detected or when no falls have been detected. The truth signal may be received from external device 40 based on patient data stored in electronic medical records, during a patient office visit, hospitalization or other time that may or may not coincide with a fall detection. In some cases, the truth signal received at block 268 may include an indication of a fall that occurred that was not detected by IMD 10.

When the truth signal indicates an undetected fall ("yes" branch of block 272), control circuit 80 may adjust a fall detection control parameter at block 274. Any of the example parameters listed above may be adjusted at block 274 in response to an undetected fall signal, however in this case the adjustment is made to make the fall detection parameters more sensitive to detecting a fall or less likely to cause a fall detection to be withheld based on a corroborating signal. For example, the directional change threshold and/or acceleration magnitude and/or slew rate threshold may be decreased, the averaging time interval for determining a body posture sample point may be increased or decreased, the fall detection window may be expanded, a filtering cut-off frequency may be increased or decreased, or a sampling rate may be adjusted to increase sensitivity for detecting falls of the given patient.

Adjustments to fall detection control parameters at block 274 may be performed in response to a single undetected fall or in response to a single false fall detection. However, in some examples, adjustments to fall detection control parameters may be made in response to a threshold number or rate of false fall detections being reached or a threshold number or rate of missed fall detections.

In some cases, the adjustments made to the control parameters at block 274 in response to a threshold number of false fall detections may depend on whether any missed fall detections have also been reported, e.g., to allow increased specificity without reducing sensitivity. The number or rate of false fall detections that triggers an adjustment of fall detection control parameters may be adjusted higher when the truth signal indicates that missed fall detections have been documented in order to avoid increasing the rate of missed fall detections. After making any adjustments as needed at block 274, control circuit 80 may return to block 254 to monitor the body posture signal and body acceleration signal according to the adjusted fall detection control parameters.

Figure 5:
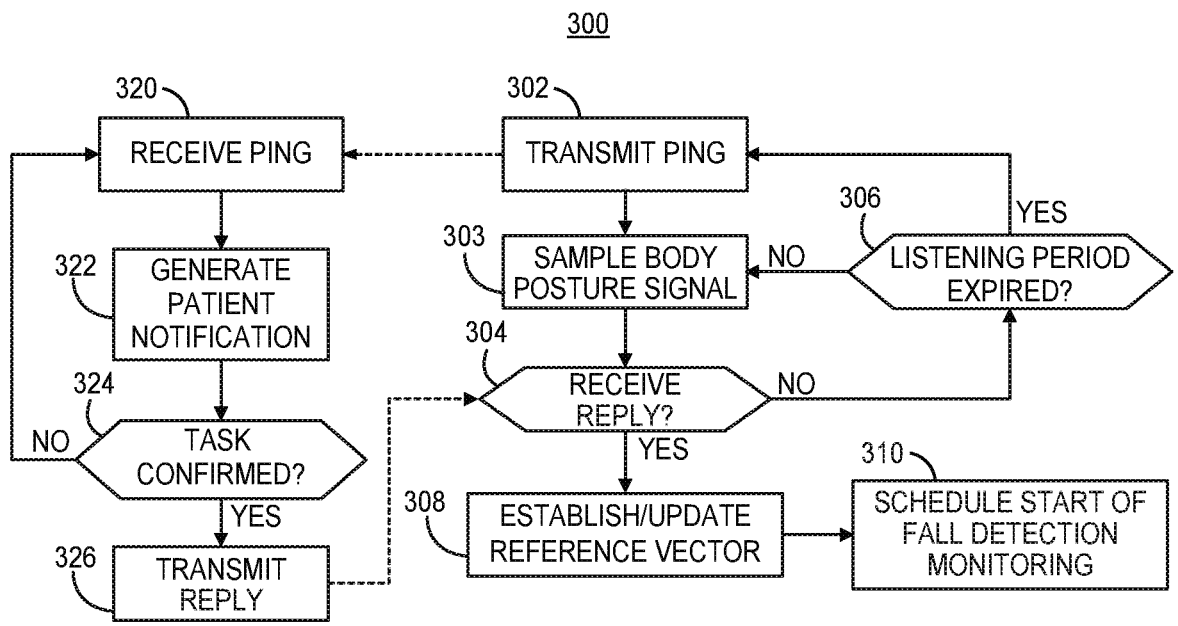
FIG. 5 is a flow chart of a method performed by a medical device for establishing a reference vector corresponding to an upright body posture according to some examples.

FIG. 5 is a flow chart 300 of a method performed by an IMD system for establishing a reference vector corresponding to an upright body posture according to some examples. At block 302, IMD 10 may transmit a wireless communication signal query or ping to an external device, such as personal device 50 shown in FIG. 1, which may be the patient's mobile smart phone as an example. IMD 10 and the patient's personal device 50 may be configured to communicate via a BLUETOOTH® pairing for instance. IMD 10 may transmit a ping to the personal device 50 and wait to receive a reply at block 304. The transmitted ping may correspond to a request to establish communication and may include a request for a reply confirming an upright task or activity. In other examples, the ping may be transmitted to establish communication and when a reply is received in response to the ping, IMD 10 may transmit a second signal requesting the that personal device 50 confirm an upright task or activity.

Meanwhile, IMD 10 may be sampling the body posture signal at block 303 and storing the sampled signal data in memory 82. In some examples, IMD 10 is determining the body posture vector by averaging the sample body posture signal over an averaging time interval as described above and storing the body posture vector at each averaging time interval.

The patient's personal device 50 may receive the transmitted ping from IMD 10 at block 320. In response to receiving the ping (and associated request to confirm an upright task or activity), the personal device 50 may be configured to generate a notification displayed to the patient, which may include an audible alert, instructing the patient to perform a task that requires being in an upright position. The patient may be notified to stand or sit in an upright position for 20 seconds (or other selected time interval) to enable IMD 10 to acquire the body posture signal during the upright position. The patient may respond to the notification by confirming that the upright position has been assumed using a touch screen or other user interface of the personal device 50. In some cases, the personal device 50 may display a timer or other prompt to guide the patient through the requested task. The personal device 50 confirms the task at block 324 based on the patient's interaction with the personal device 50 and transmits a reply at block 326 confirming that the patient assumed an upright position.

When the personal device 50 does not receive a confirmation from the patient that the task has been performed within a predetermined time limit, e.g., within ten minutes or less, or within five minutes or less, the personal device 50 may cancel the notification and wait for the next ping from IMD 10. IMD 10 may be configured to listen for a reply at block 304 for a limited listening period, e.g., for ten minutes or less or five minutes or less, in order to reduce current drain of power source 98. Personal device 50 may transmit the reply at 326 repeatedly during the predetermined listening period when the task is confirmed so that the telemetry circuit 88 may go to sleep and wake up to listen repeatedly during the listening period until a reply is received at block 304 or the listening period expires at block 306. If the listening period expires without receiving a reply, IMD 10 may wait one day, several hours, one hour or other scheduled time period and transmit a ping again at block 302 to reattempt confirmation of an upright posture in cooperation with personal device 50.

In response to receiving a reply at block 304, IMD 10 establishes the reference vector at block 308. The reference vector may be the most recently stored body posture vector, the next body posture vector determined after receiving the reply, or a combination of two or more body posture vectors sampled within a time window of the reply. In some examples, upon receiving the reply, IMD 10 begins an averaging window over which the body posture signal is averaged for determining a reference vector corresponding to an upright position or posture. Once the reference vector is established or updated at block 308, telemetry circuit 88 may not transmit a ping at block 302 again until a scheduled update period has elapsed, e.g., one week or other scheduled time period.

In other examples, the process of FIG. 5 may involve a third device, such as an appliance 52 (shown in FIG. 1) that is configured to communicate with the patient's personal device 50. In response to receiving the query ping at block 320, the personal device 50 generates a patient notification at block 322 instructing the patient to perform a task using the appliance 52. The personal device 50 may pair with another device, e.g., a BLUETOOTH enabled appliance 52 as shown in FIG. 1, when the patient performs the instructed task. In an illustrative example, the appliance 52 may be a weighing scale. The patient's personal device 50 may generate a notification instructing the patient that it is time to weigh himself or herself. Upon stepping on the weighing scale, the scale and personal device 50 may pair and establish a link 54 (as shown in FIG. 1) so that the personal device 50 can receive the patient's weight from the weighing scale and confirm that the task, requiring the patient to be in a standing upright position, is performed (block 324). In response to confirming the upright posture task based on communication with the appliance 52, the personal device 52 may transmit a reply back to IMD 10 at block 326. IMD 10 receives the reply at block 304 and establishes the reference vector at block 308 using the body posture signal sampled over a time period coinciding with the confirmed upright posture task. For instance, personal device 52 may transmit a time stamp of when the patient was performing the upright task in the reply to IMD 10, allowing control circuit 80 to identify a sampled body posture vector stored in memory having a corresponding time stamp.

In another example, the IMD 10 may ping the personal device 50 at a scheduled time of day when the patient is expected to be performing an upright posture task or activity, such as daily exercise on a treadmill or walking or sitting in a car. The personal device 50 may be paired with an appliance 52 associated with the daily activity, such as an activity tracker or a BLUETOOTH® audio system of a car. The personal device 50 may transmit a reply back to the IMD 10 at block 326 to confirm that the patient is engaged in the daily activity, such as walking or sitting in the car. IMD 10 establishes the reference vector at block 308 by acquiring the body posture signal in response to the reply.

In some examples, receiving a reply from personal device 50 indicating the patient is riding or driving in a car, based on the personal device 50 being paired with the car audio system, may cause the IMD 10 to temporarily disable fall detection since the patient is unlikely to experience a fall and disabling the fall detection may conserve power source 88. In this case, control circuit 80 may disable fall detection and schedule a time to restart fall detection monitoring at block 310. The time duration that fall detection is disabled may be fixed or programmable and may be tailored for a given patient, e.g., based on data extracted from the personal device 50 relating to average travel or commuting time. In some examples, fall detection is disabled until a signal is received by IMD 10 from personal device 50 indicating that it is no longer paired with the car audio system or detecting that the patient is moving in a car.

Figure 6:
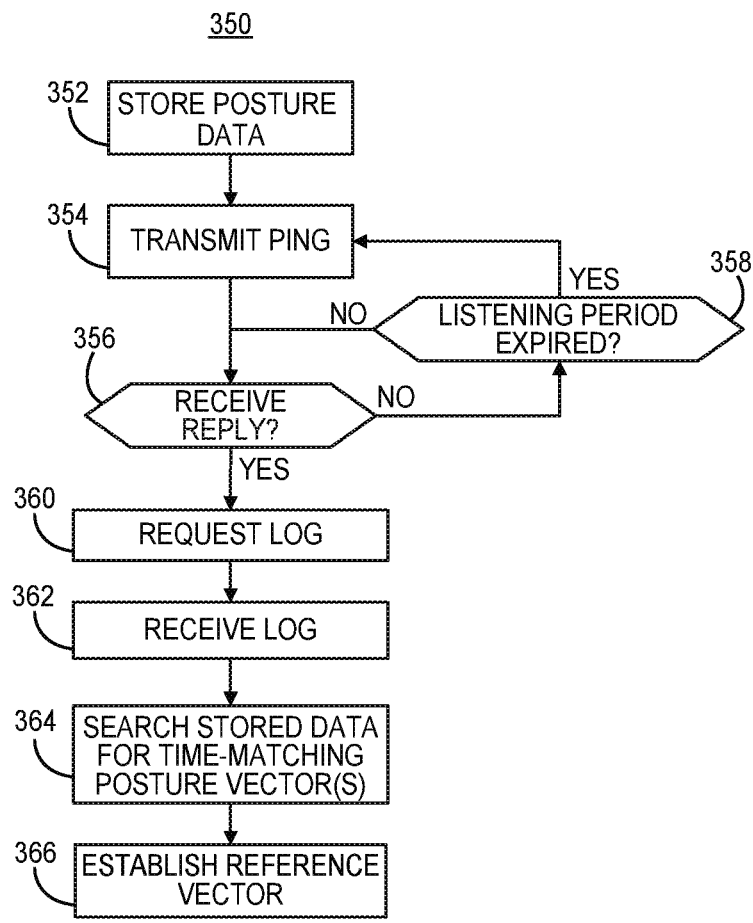
FIG. 6 is a flow chart of a method performed by the system of FIG. 1 for establishing a reference vector corresponding to an upright posture according to another example.

FIG. 6 is a flow chart 350 of a method performed by the IMD system of FIG. 1 for establishing a reference vector corresponding to an upright posture according to another example. At block 352, accelerometer circuit 90, control circuit 80 and memory 92 cooperatively store body posture signal data on an ongoing basis according to a monitoring protocol as described above. For example, a body posture vector may be determined by control circuit 80 and stored in memory 82 after every n-second averaging interval. At block 354, IMD telemetry circuit 88 may transmit a ping to an external device, such as personal device 50, and wait for a reply at block 356. If a listening period expires before the reply is received ("yes" branch of block 358), control circuit 80 may return to block 354 to wait for a scheduled time interval after which telemetry circuit 88 may repeat transmitting the ping. The ping may be transmitted repeatedly over a predetermined time interval, e.g., ten minutes or less, and if no reply is received by telemetry circuit 88, control circuit 80 may wait for one hour, several hours, one day or other scheduled time period before controlling the telemetry circuit 88 to transmit another ping.

When IMD telemetry circuit 88 receives a reply from the personal device 50 at block 356, telemetry circuit 88 may establish a communication link with the personal device 50 and transmit a log request to the personal device 50 at block 360. The patient's personal device 50 may acquire a log of a patient activity that corresponds to an upright position, along with time and date information. The personal device 50 may transmit log data to the IMD 10 upon request.

For instance, the patient may use a weighing scale that transmits the weight to the personal device 50. Personal device 50 stores the weight with a time and date stamp. In some cases, the patient may be following a prescribed weighing schedule, for example daily weighing, when the patient is taking a diuretic, suffering from heart failure or for another medical reason, such that weight data acquired regularly is stored in the personal device 50. In another example, the personal device 50 may include a mileage tracking app that tracks times that the patient is riding in a car. Time and date data corresponding to when the patient is in a car, most likely sitting in an upright position, may be stored in a log in personal device 50. In yet another example, personal device 50 may log activity or receive activity tracking from another appliance, such as a wrist worn activity tracker. For instance, personal device 50 may log steps (during walking) taken by the patient over the course of a day. The activity log may include date and time stamps taken when the patient is detected to be walking (or jogging) and in an upright position. Various logs of a patient activity associated with an upright position may be obtained directly by personal device 50 or retrieved from an appliance 52 and stored by personal device 50.

IMD 10 receives, via telemetry circuit 88, the log data at block 362. Control circuit 80 searches the stored body posture data at block 364 to match one or more time and date stamps in the received log data to time and date stamps of the stored body posture vectors. One or more body posture vectors obtained at a time and date matching a time and date stamp in the log data may be used to establish the reference vector by control circuit 80 at block 366. When more than one body posture vector is identified by control circuit 80 as having a time and date stamp that matches an upright activity log time and date, multiple body posture vectors may be averaged or used in combination by control circuit 80 to establish the reference vector. In other examples, a single body posture vector having a time and date stamp matching a logged activity time and date stamp may be stored in memory 82 as the reference vector.

A time and date stamp of a body posture vector may be determined to match a logged activity time and date stamp when the two stamps are within a predetermined time interval of each other, e.g., within 10 seconds or less or within 5 seconds or less. In other examples, additional criteria may be applied in selecting one or more stored body posture vectors having time and date stamps matching logged activity data. For example, criteria relating to time of day, patient physical activity metric, heart rate, or other criteria may be applied for accepting a body posture vector as a valid vector for use in establishing the reference vector.

Figure 7:
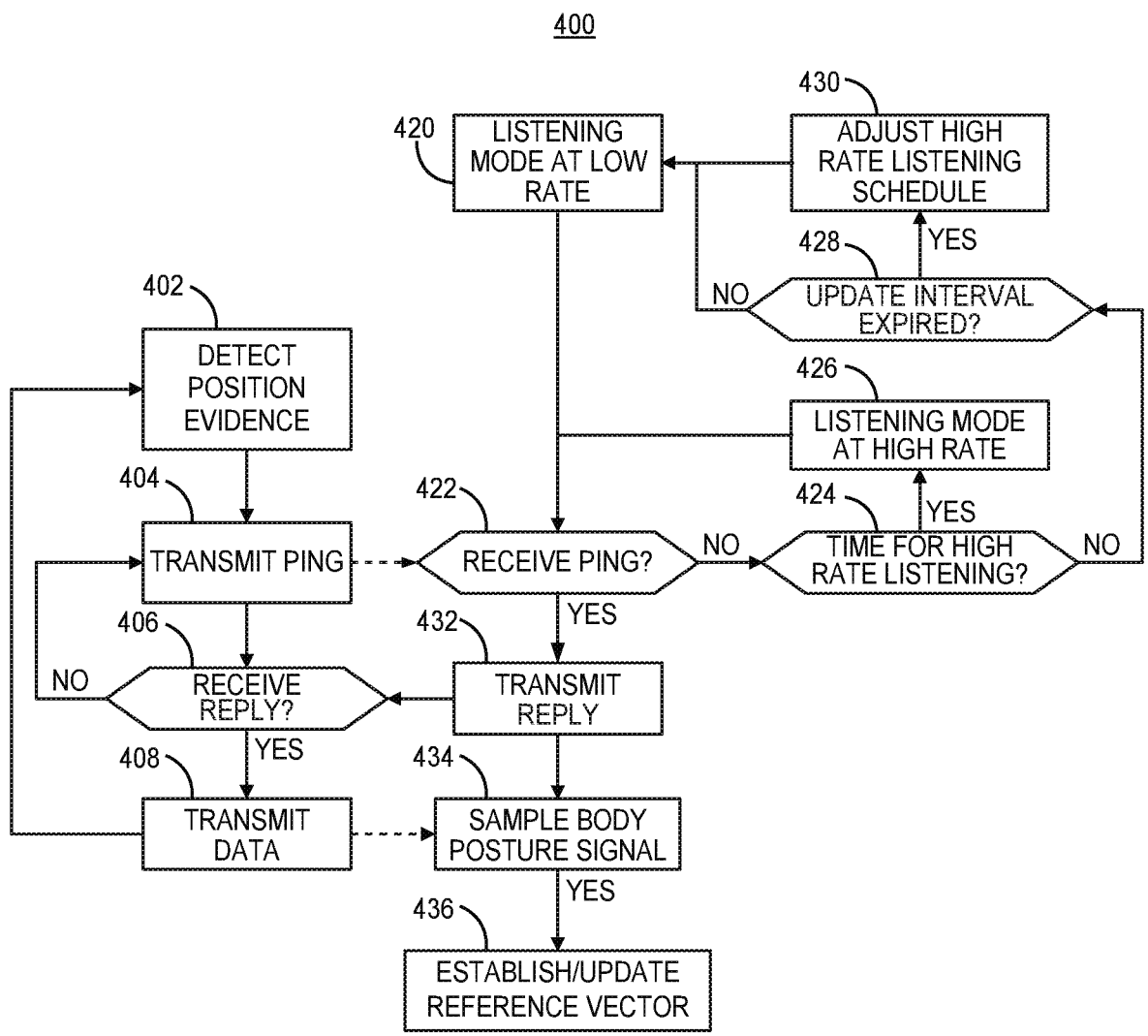
FIG. 7 is a flow chart of a method for establishing a reference vector by the medical device system of FIG. 1 according to another example.

FIG. 7 is a flow chart 400 of a method for establishing a reference vector by the medical device system of FIG. 1 according to another example. The processes of FIGS. 5 and 6 both include communication between IMD 10 and an external device being initiated by IMD 10 transmitting a ping via telemetry circuit 88. Current drain of power source 98 may be conserved by avoiding powering up IMD telemetry circuit 88 in a listening mode for receiving a ping from an external device initiating a communication session. However, it is contemplated that an external device, e.g., external device 40 or personal device 50, may initiate communication with IMD 10 by transmitting a ping to IMD telemetry circuit 88 for establishing a communication link.

At block 402 in FIG. 7, an external device may detect or receive body position evidence or information. For example, personal device 50 may detect walking or be paired with an appliance associated with an upright position. In other examples, the external device may accumulate a log of data with time and date stamps, such as driving mileage or patient weight. The external device may transmit a ping at block 404 to request communication with the IMD 10. Meanwhile, at block 420, IMD control circuit 80 may be controlling IMD telemetry circuit 88 to wake up at a first, relatively low rate, e.g., once per hour and remain in a listening mode for a predetermined period of time.

If the IMD telemetry circuit 88 has not received a transmitted ping (block 422), control circuit 80 may determine if it is time to increase the listening rate at block 424. At block 426, control circuit 80 may increase the frequency of waking up telemetry circuit 88 for listening for a ping at scheduled times of day and/or when a threshold level of physical activity is detected based on the patient physical activity signal, for example. If it is time to increase the listening rate, control circuit 80 wakes up telemetry circuit 88 more frequently, e.g., once per minute or more often for a predetermined interval of time, e.g., ten to fifteen minutes, to listen for a ping. If no ping is received, the control circuit 80 may switch back to waking up the telemetry circuit 88 at the lower rate for listening for a ping.

At block 428, control circuit 80 may determine if a reference vector update interval has expired, for example three to five days, one week, two weeks or other selected minimum update interval. When a ping has not been received for establishing or updating the reference vector for an extended period of time ("yes" branch of block 428), control circuit 80 may adjust the scheduled time of day for switching to a high rate of waking up telemetry circuit 88 at block 430. For example, the patient may be expected to weigh themselves, be riding in a car, or be walking at certain times of day, according to habit, when the high wake up rate is scheduled to occur at block 426. If a ping has not been received by telemetry circuit 88 for causing control circuit 80 to update the reference vector before the update interval expires at block 428 (since the last update), the scheduled time of day for starting the increased wake up rate at block 426 may be adjusted at block 430, e.g., shifted by 10 to 15 minutes earlier or later, one hour earlier or later or other time interval shift, in an attempt to increase the likelihood of receiving the expected ping from an external device for confirming that the patient is engaged in an activity that involves an upright position.

Once the ping is received at block 422, control circuit 80 may sample the body posture signal at block 434 based on the ping being an indication that the patient is currently engaged in an upright activity. Control circuit 80 may establish or update the reference vector at block 436 based on a currently sampled body posture signal in response to receiving the ping. In some examples, the body posture vector may be sampled at multiple successive time points at block 434 to verify a stable body posture vector before establishing a new reference vector. If a stable body posture vector cannot be verified by control circuit 80, e.g., based on successively sampled body posture vectors being within a threshold difference of each other, a previously established reference vector may remain stored in memory 82 as the current reference vector at block 436.

Control circuit 80 may identify a currently sampled body posture vector as "stable" by comparing it to a previously stored body posture vector and/or a previously established reference vector to verify that a difference in the direction of the currently sampled body posture signal and the previously stored body posture vector and/or previously stored reference vector is within a difference threshold, indicating that the body posture vector is stable. If the currently sampled body posture vector is more than a difference threshold from a previously stored body posture, the currently sampled body posture vector may or may not be stored in memory 82. In some examples, the currently sampled body posture vector is stored for use in verifying a subsequent body posture vector as being stable for updating the reference vector at a later time point. However, until the sampled body posture vector(s) are verified to be stable, e.g., within a difference threshold of a previous reference vector or previously sampled body posture vector, the previously established reference vector may continue to be used as the updated reference vector at block 436. Once control circuit 80 determines that a currently sampled body posture vector is stable relative to a preceding body posture vector, the reference vector may be updated based on the currently sampled body posture vector at block 436.

In some examples, telemetry circuit 88 may transmit a reply back to the sending device at block 432 in response to receiving the ping at block 422 to establish two-way communication. The external device 40 or personal device 50 may receive the transmitted reply at block 406 and transmit a signal at block 408 indicating that the patient is engaged in an upright activity or transmit an accumulated data log that includes date and time stamps associated with a task or activity involving an upright posture. The control circuit 80 may search body posture vectors previously stored in memory 82 for matching time and date stamps at block 434, instead of using a currently sampled body posture signal, for establishing or updating the reference vector at block 436.

In addition to or instead of waiting for a ping from IMD 10 as described in conjunction with FIGS. 5 and 6, the personal device 50 may be configured to transmit a ping to IMD 10 at block 404 repeatedly when an upright activity is identified (e.g., based on a pairing with another appliance 52) or when an updated log corresponding to an upright activity is available. Control circuit 80 may be configured to wake up telemetry circuit 88 to listen for a ping at block 422. During certain times of day, control circuit 80 may be configured to wake up telemetry circuit 88 to listen for the ping at a higher rate than during other times of day.

Figure 8:
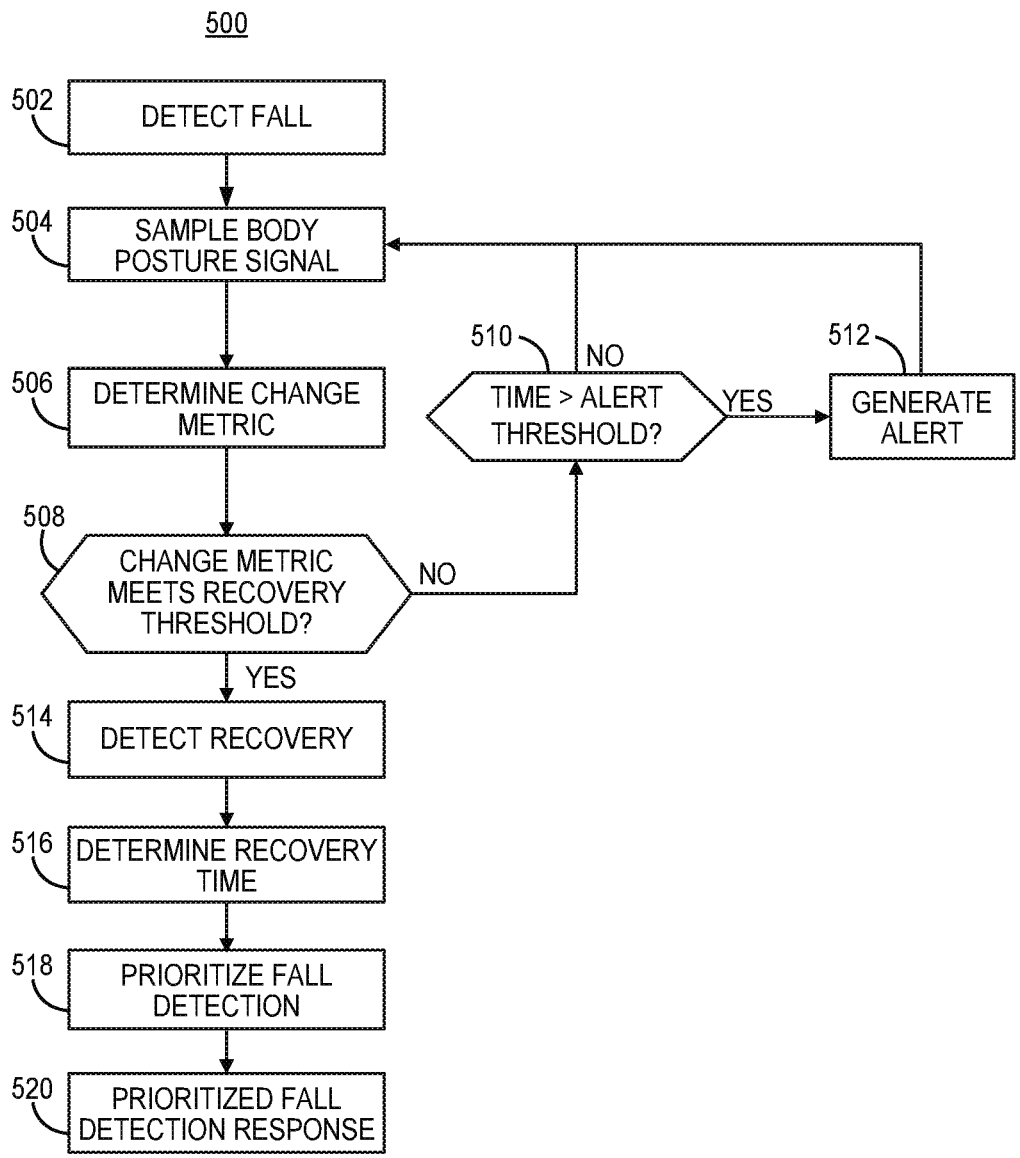
FIG. 8 is a flow chart of a method performed by a medical device for determining a recovery time following a fall detection.

FIG. 8 is a flow chart 500 of a method that may be performed by IMD 10 for determining a recovery time following a fall detection. At block 502, control circuit 80 detects a fall, e.g., as described in conjunction with FIG. 4. Control circuit 80 continues to monitor the body posture signal at block 504. Control circuit 80 may determine a body posture vector at the end of each n-second averaging interval. The n-second averaging interval may be the same averaging interval used in monitoring the body posture signal prior to fall detection or a shorter interval, e.g., 0.25 seconds, 0.5 seconds or 1 second, in order to enable greater time resolution in determining the time to recover after the fall.

At block 506, control circuit 80 determines a directional change metric correlated to the angle between the fall detection body posture vector and the current, post-fall detection body posture vector. The fall detection body posture vector is the body posture vector that satisfied the directional change threshold at block 258 of FIG. 4, leading to a fall detection. If the directional change metric between the current post-fall body posture vector and the fall detection body posture vector does not meet a recovery threshold, as determined at block 508, recovery from the fall is not detected. A posture change that does not meet the recovery criteria indicates that the patient may still be lying on the ground and has not recovered from the fall.

In other examples, control circuit 80 may additionally or alternatively determine a directional change metric correlated to the angle between the reference vector and the post-fall detection body posture vector at block 506. When the directional change between the post-fall detection body posture vector and the reference vector is less than a specified change threshold from, recovery may be detected at block 514. A directional change metric between the reference vector and the post-fall detection body posture vector that is less than a change threshold may indicate that the patient has recovered and returned to the pre-fall body posture. When the directional change metric between the post-fall detection body posture vector and the reference vector is still greater than a change threshold, the patient may be still on the ground or rolling on the ground following a fall. Accordingly, at block 508, control circuit 80 may require that a directional change metric between the fall detection body posture vector and the post-fall detection body posture vector is greater than a recovery threshold and/or a directional change metric between the reference vector and the post-fall detection body posture vector is less than a recovery threshold.

When the recovery criteria are not met at block 508, control circuit 80 may compare the time since the fall detection to an alert threshold at block 510. For example, control circuit 80 may start a timer upon fall detection and compare the time since fall detection to the alert threshold time interval. If the fall is severe, the patient may be injured or unconscious and need assistance. Control circuit 80 may determine that if recovery has not been detected and alert threshold time interval expires at block 510, an alert may be generated at block 512. Control circuit 80 may control telemetry circuit 88 to transmit an alert to an external device, e.g., external device 40 or personal device 50, to trigger an alarm and/or transmit a message by text, phone call, email or other means to a first responder, call center, clinician or other caregiver.

If the alert threshold time interval has not expired or an alert has been generated, control circuit 80 continues to sample the body posture signal at block 504 to detect recovery. When the directional change between the current post-fall body posture vector and the fall detection body posture vector meets recovery criteria, as determined at block 508, recovery from the fall is detected at block 514. Control circuit 80 determines the recovery time at block 516 as the time interval (which may be based on the number of averaging intervals of the body posture signal) from fall detection to recovery detection. At block 518, control circuit 80 may use the recovery time to prioritize the fall detection relative to other fall detections for data storage and reporting purposes. In some cases, the recovery time may be so short (e.g., one second or less) that a fall detection is cancelled, withheld or labeled false detection even when patient body posture and signal spike detection criteria for detecting a fall are satisfied. In other examples, control circuit 80 may identify the fall as a low priority fall in response to a very short recovery time. The recovery time determined at block 516 may be compared to one or more fall recovery time thresholds for prioritizing the fall detection at block 518. A fall recovery time threshold may be a previously determined fall recovery time such that a fall detection having a greater recovery time than another fall detection is given higher priority at block 518. Control circuit 80 may generally prioritize fall detections based on the recovery time with greater recovery time corresponding to a more severe, higher priority fall detection for data storage, reporting or other fall detection response purposes.

At block 520, control circuit 80 performs a fall detection response in accordance with the prioritization determined at block 518. For example, if a previously detected fall had a shorter recovery time than the currently determined recovery time, the fall detection data for the previous fall may be overwritten by fall detection data acquired for the currently detected fall. If the recovery time exceeds a severity time threshold (which may be less than the alert threshold time interval applied at block 510), control circuit 80 may control telemetry circuit 88 to transmit a notification to an external device to notify a clinician and/or patient that a medical examination for checking for injuries and/or patient follow-up or clinical review of the fall data may be warranted for managing treatment of a medical condition, prescribed medication adjustment, etc. Fall data that may be determined by control circuit 80 and stored in memory 82 for transmission and review may include trends in fall data, such as frequency of fall detections and/or trend in fall severity based on the trend in fall recovery time durations so that a clinician can recognize if the patient is falling more often and/or suffering more severe falls, for example.

When the recovery time is less than previously stored fall detection data, and memory allocated for storing complete sets of fall detection data is full, the response at block 520 may include storing a limited amount of fall detection data, such as the detection with a time and date stamp, without or with limited additional signal data or other information. No notifications or alerts may be transmitted by telemetry circuit 88 at the time of the fall detection if the recovery time is relatively quick, e.g., within a few seconds or less than a short recovery time threshold such as 10 seconds or less.

Figure 9:
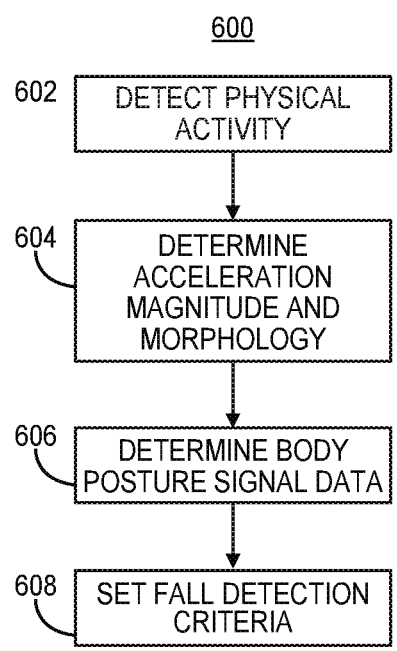
FIG. 9 is a flow chart of a method performed by a medical device for setting or adjusting fall detection control parameters according to some examples.

FIG. 9 is a flow chart 600 of a method that may be performed by IMD 10 for setting or adjusting fall detection control parameters according to some examples. IMD 10 may perform the method of 600 upon initial implant of IMD 10 or when fall detection is first turned on to establish fall detection criteria for detecting a patient fall. IMD 10 may perform the method of 600 to adjust fall detection criteria, e.g., at block 274 of FIG. 4, after a truth signal is received indicating that a false fall detection or a missed fall detection occurred.

At block 602, control circuit 80 monitors the accelerometer signal for determining a patient physical activity metric. As described above, a bandpass filtered accelerometer signal (which may be a combination of one, two or all three axis component signals) may be passed to control circuit 80 as a patient physical activity signal. Control circuit 80 may analyze the patient physical activity signal for determining a metric of patient physical activity, e.g., by determining an activity count correlated to the level of patient physical activity at predetermined time intervals, e.g., every two seconds. Control circuit 80 may detect patient physical activity at block 602 that is greater than a predetermined threshold, e.g., activity metrics that are greater than an ADL threshold. An activity metric greater than the ADL threshold may represent patient activity that could occur with changes in posture and relatively high peaks in the body acceleration signal, potentially leading to a false fall detection when the spike detection and body posture change criteria are met during normal patient activity. The behavior of the accelerometer signal during normal patient physical activity may be used as an indication of what a lower boundary of a magnitude threshold and slew rate thresholds or frequency thresholds applied to the body acceleration signal for fall detection should be. In some patients, a fall may occur relatively slowly with multiple, relatively lower magnitude peaks in the body acceleration signal, for example when a patient stumbles and tries to regain footing or catch themselves during the fall but ultimately falls. In other cases, the fall may be sudden with a single large impact, e.g., if a patient experiences syncope and loses muscle control. Accordingly, characterizing the individual patient physical activity accelerometer signal during detected patient activity and using previous fall detection data if available can enable IMD 10 to set fall detection criteria to improve sensitivity and/or specificity of fall detection.

At block 604, control circuit 80 may determine the peak magnitude of the body acceleration signal (or one or more of the x-, y- and z-signal components) during the detected patient physical activity. In some examples, control circuit 80 may determine a morphology or waveform shape of the body acceleration signal obtained from one or more axes during the detected physical activity. Control circuit 80 may process the body acceleration signal to detect the magnitude, slew rate, frequency, a cadence of signal peaks or other characteristic features of the body acceleration signal morphology during the period of activity.

Control circuit 80 may additionally or alternatively determine body posture signal data at block 606 during the detected patient physical activity. Control circuit may determine characteristics of the body posture signal such as signal x-, y- and/or z-component magnitudes, resultant body posture vector magnitude, and/or a maximum body posture vector directional change relative to a reference vector during the detected patient physical activity. Characterizing the body posture signal data during the detected physical activity may guide selection of the body posture directional change threshold and other fall detection criteria by control circuit 80.

At block 608, control circuit 80 may set the fall detection criteria based on the analysis of the body posture signal data and the body acceleration signal data determined during detected patient physical activity. Control circuit 80 may set a directional change threshold based on maximum directional change in the body posture signal detected during the patient activity, which may be within a time interval corresponding to the fall detection window or a specified number of body posture signal averaging windows. Control circuit 80 may further set other body posture criteria such as a threshold directional change that is not a change that is determined from a specified starting x-, y- and z-components of a body posture vector associated with normal patient activity or specified ending x-, y- and z-components of the body posture vector that may be associated with body postures assumed during normal patient activity. Body acceleration signal spike detection criteria may be set to avoid detecting acceleration signal spikes that occur during the normal patient physical activity. Fall detection criteria to be applied to the body acceleration signal for spike detection may be set based on the analysis of the body acceleration signal during the detected patient activity to exclude detecting a spike having a morphology that matches spikes during the normal patient activity. Fall detection criteria may be set to avoid a false fall detection during normal physical activity. For example, control circuit 80 may set the magnitude threshold applied to the body acceleration signal to be greater than a maximum magnitude of the body acceleration signal during the patient's normal physical activity. If true fall detection data is available, the signal spike magnitude(s) and body posture change metric(s) acquired during the true fall detection(s) may be compared to the maximum body acceleration signal magnitude and maximum body posture change during normal physical activity so that the acceleration signal magnitude threshold and the posture vector directional change threshold may be set below the lowest respective values corresponding to a true fall detection and above the maximum respective values during normal physical activity of the patient.

When there is confounding data representing true fall detections or missed fall detections having body acceleration signal magnitude and/or body posture signal characteristics that overlap with corresponding characteristics determined during the normal physical activity, the morphology of the body acceleration signal may be used to differentiate a fall from patient physical activity. For example, fall detection criteria may be set relating to the slope, cadence, frequency power spectrum, overall morphology of the acceleration signal waveform or other features of the body acceleration signal to discriminate between patient physical activity and a patient fall based on the morphology of the body acceleration signal. The morphology of the body acceleration signal may be acquired during normal patient physical activity, which may include ADL or more strenuous activity and stored for comparison to a potential signal spike during fall detection monitoring. A fall detection spike may be detected based on a morphology that does not match the body acceleration signal morphology acquired during normal physical activity. Detecting a non-matching morphology may be based on wavelet analysis, slopes, area, determining differences between time aligned sample points, frequency domain analysis or other methods.

Figure 10:
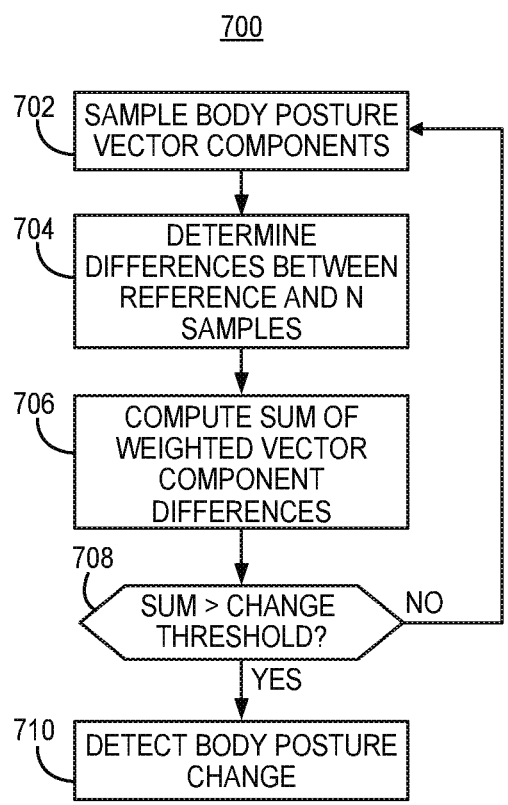
FIG. 10 is a flow chart of a method that may be performed by a medical device for detecting a body posture change according to some examples.

FIG. 10 is a flow chart 700 of a method that may be performed by IMD 10 for detecting a body posture change according to some examples. The method of flow chart 700 does not require establishing a reference vector corresponding to an upright position. A reference vector in the method of FIG. 10 is a sampled body posture vector at a time point earlier than a currently sampled body posture vector. A relative change in body posture vector direction between the previously sampled body posture vector and the current body posture vector is determined according to a directional change metric and compared to a threshold. The method of FIG. 10 is useful in detecting a body posture change corresponding to a fall that does not necessarily originate from an upright position, e.g., rolling out of bed or falling from a leaning or bending position.

At block 702, control circuit 80 samples the body posture signal to obtain each of the x-, y- and z-components of the body posture signal at a selected sampling rate, which may include averaging the sampled signal components over an averaging window, e.g., over 0.25 seconds, 0.5 seconds, 1 second, 2 seconds or other averaging window. In one example, each x-, y-, and z-magnitude component of a sampled body posture vector may be determined by averaging sampled points of each of the x-axis signal, y-axis signal and z-axis signal of accelerometer 12 over an averaging window, where the sampling rate is 32 Hz and the averaging window is 0.5 seconds, providing the x(i), y(i) and z(i) magnitude components of the body posture vector every 0.5 seconds. It is recognized that other sampling rates and averaging windows may be selected.

In the examples described in conjunction with FIG. 10, a three-dimensional body posture vector is monitored such that each of the x-, y- and z-axis component signals are analyzed as the component signals of the three-dimensional resultant body posture vector. However, it is recognized that the method of FIG. 10 may be implemented using one or two axis signals instead of all three axis signals for detecting a body posture change in one or two axis directions.

At block 704, control circuit 80 determines differences in magnitude between a reference vector component and a respective body posture vector component sampled n averaging windows after the reference vector. For example, the reference vector may be referred to as the $i^{th}$ body posture vector having x(i), y(i), and z(i) components. A subsequently sampled body posture vector may be identified as the i+n body posture vector, obtained n averaging windows after the reference vector. Each of the i+n body posture vectors include an x(i+n), y(i+n) and z(i+n) component magnitude.

At block 704, control circuit 80 determines a difference between the reference vector component magnitudes and the subsequent sampled body posture vector component magnitudes for each one of n subsequently sampled body posture vectors, where n is the number of averaging windows after the reference vector. In one example, control circuit determines the magnitude differences for each vector component between the reference vector and four subsequently obtained body posture vectors (n=1 to 4). For example, control circuit 80 may determine the differences x(i)–x(i+1), x(i)–x(i+2), x(i)–x(i+3) and x(i)–x(i+4) for the x-axis and similarly determine four differences between the y(i) and z(i) reference components and each one of four y(i+n) and z(i+n) body posture vector components, respectively, where n equals 1 to 4. The reference vector and four subsequent body posture vectors may include five consecutively sampled body posture vectors obtained over a two-second time interval, as an example, with the first of the five consecutively sampled body posture vectors being the reference vector.

At block 706, a weighted sum of the vector component differences is determined for each of the n body posture vectors following the reference vector, corresponding to n different time points following the reference vector. In one example, the magnitude of the reference vector component may be used as a weighting factor that is multiplied by each of the n differences determined for that vector component. The products of each reference vector component magnitude and the determined n vector component differences for each of the x-, y- and z-axes are summed together to determine a metric of the directional change of the body posture vector at each of the n time points. For example, the directional change metric at the time point corresponding to n=1, e.g., one averaging interval after the reference vector, may be computed as:

$$\text{Metric}(1) = X(\text{ref}) * \Delta x(1) + Y(\text{ref}) * \Delta y(1) + Z(\text{ref}) * \Delta z(1)$$

where X(ref), Y(ref) and Z(ref) each represent the magnitude of the respective x-, y- and z-components of the reference vector and $\Delta x(1)$ is the magnitude difference x(i)–x(i+1), $\Delta y(1)$ is the magnitude difference y(i)–y(i+1) and $\Delta z(1)$ is the magnitude difference z(i)–z(i+1).

This directional change metric may be determined for each of n time points using the reference vector component magnitudes and each of the x(i+n), y(i+n) and z(i+n) vector components of the subsequent n body posture vectors. For example, a directional change metric, Metric(n), may be determined for the reference vector and each one of four subsequent body posture vectors obtained at 0.5 second intervals. In addition to Metric(1) determined above, the following three directional change metrics may also be determined based on the same reference vector obtained at time point i:

$$\text{Metric}(2)=X(\text{ref})*\Delta x(2)+Y(\text{ref})*\Delta y(2)+Z(\text{ref})*\Delta z(2)$$

$$\text{Metric}(3)=X(\text{ref})*\Delta x(3)+Y(\text{ref})*\Delta y(3)+Z(\text{ref})*\Delta z(3)$$

$$\text{Metric}(4)=X(\text{ref})*\Delta x(4)+Y(\text{ref})*\Delta y(4)+Z(\text{ref})*\Delta z(4)$$

At block 708, control circuit 80 may determine if any of the n directional change metrics is greater than a change threshold. When at least one of the directional change metrics determined over n averaging intervals is greater than the change threshold, a body posture change corresponding to a patient fall is detected at block 710. These sequential directional change metrics, each based on a weighted sum of body posture vector component differences, may be determined at block 256 of FIG. 4 and the body posture change detection may be made at block 258 based on at least one of these directional change metrics exceeding a change threshold. For example, the change threshold may be set such that at least one vector component difference is required to change by at least 20% to 80% of the reference vector.

When a body acceleration signal spike is detected within a fall window of the detected body posture change, a fall may be detected as described above in conjunction with FIG. 4. In some examples, control circuit 80 may monitor the body acceleration signal to detect a body acceleration signal spike then analyze the body posture signal for detecting a body posture change within a fall window of the detected signal spike using the technique of FIG. 10. For example, the reference vector may be derived from the body posture signal at a predetermined time interval prior to the detected body acceleration signal spike and each of the subsequent n body posture vectors may be obtained at each one of n averaging windows following the reference vector time point such that the n body posture vectors span the spike detection. For instance, the reference vector may be determined over an averaging interval that is two to six seconds prior to the body acceleration signal spike detection and the subsequent n body posture vectors may include two to six body posture vectors sampled after the body acceleration signal spike detection.

This technique of determining a directional change metric as the sum of weighted vector component differences may be independent of changes in IMD 10 orientation relative to the patient's body that may occur over time. The directional change metric determined at block 706 may be correlated to an angle between the reference vector and the vector at the i+n time point but independent of a change in the accelerometer axes relative to the direction of gravity due to rotation of the IMD 10 in the patient's body. The technique of FIG. 10 may provide greater sensitivity to detecting a fall that involves a sequence of body posture changes that may occur during rolling, stumbling or tumbling. While this technique for detecting a body posture change is described for the purposes of detecting a fall, it is recognized that detecting a body posture change using the technique of FIG. 10 may be performed post-fall detection for detecting postural changes of the patient after the fall, such as rolling on the ground for confirming a patient fall. When the accelerometer axes are oriented such that the x-axis is vertical when the patient is in an upright position, the greatest changes in magnitude of the body posture vector components may occur in the y- and z-axes during rolling. Accordingly, in some examples, the method of FIG. 10 may be enabled post-fall detection using the y- and z-axes (or radial axes as opposed to a vertical axis with respect to an upright body position) for detecting rolling on the ground and distinguishing rolling from a posture change and physical activity that indicates fall recovery.

In some examples, the method of FIG. 10 may be enabled during night time hours or when the patient is expected to be asleep for detecting a fall from rolling out of bed. In some examples, the magnitude of a radial axis component that is close to 1, e.g., the y-axis signal component or the z-axis signal component, which may be relatively close to zero when the patient is upright, may be used as a trigger for enabling the method of FIG. 10. For instance, a high magnitude (close to 1) of the y- or z-axis component may indicate that the patient is lying down or bent or leaning over. If this high magnitude is sustained for a specified duration, e.g. one minute, then the method of FIG. 10 may be enabled for detecting a rolling fall out of bed. A different directional change metric, e.g., as described above in conjunction with FIG. 4, may be determined and compared to a respective directional change threshold during daytime hours or when the patient is expected to be awake and active for detecting a body posture change from an upright posture meeting fall detection criteria.

Control circuit 80 may determine a directional change metric according to one method during one portion of a 24-hour period and determine a different directional change metric according to a different method during a second portion of the 24 hour period. In this way, control circuit 80 can detect a body posture change from an upright to a non-upright position during the first portion of the 24-hour period when the patient is expected to at risk for falling from an upright position and detect a body posture change from a non-upright to a non-upright position during the second portion of the 24-hour period when the patient is expected to be in a laying position and at risk for falling from the laying position, e.g., by rolling out of bed. Control circuit 80 may switch between determining the first directional change metric and the second direction change metric one or more times per day based on time of day or based on detecting a high (or low) magnitude of an accelerometer axis signal component corresponding to a horizontal (or upright) position.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single module or unit for purposes of clarity, it should be understood that the techniques of this disclosure may be performed by a combination of units or modules associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device comprising:
  an accelerometer circuit configured to produce an accelerometer signal and generate a body posture signal and a body acceleration signal from the accelerometer signal;
  a control circuit configured to receive the body posture signal and the body acceleration signal and:
    determine that the body posture signal and the body acceleration signal meet fall detection criteria by:
      determining a first body posture vector from the body posture signal at a first time point;
      determining a second body posture vector from the body posture signal at a second time point later than the first time point of the first body posture vector;
      determining a directional change metric correlated to an angle between the first body posture vector and the second body posture vector;
      determining that the directional change metric is greater than a threshold directional change;
      detecting an acceleration signal spike from the body acceleration signal; and
      determining that the acceleration signal spike and the second time point are within a fall time window of each other;
    detect a patient fall in response to the body posture signal and the body acceleration signal meeting the fall detection criteria;
    determine a third body posture vector at a third time point after the second time point determine a directional change metric between the third body posture vector and at least one of the first body posture vector and the second body posture vector;
    determine that the directional change metric meets fall recovery criteria;
    determine a fall recovery time as a time interval from the second time point to the third time point in response to the directional change metric meeting the fall recovery criteria; and
    determine at least one of a trend in a frequency of fall detections and a trend in fall recovery time durations in response to detecting the patient fall; and
  a telemetry circuit configured to:
    transmit the determined trend;
    receive a first truth signal transmitted from another device, the truth signal indicating that the detected patient fall is a falsely detected patient fall,
    responsive to the telemetry circuit receiving the first truth signal, the control circuit being further configured to adjust at least one fall detection control parameter used to control at least one of: generating the body posture signal from the accelerometer signal; generating the body acceleration signal from the accelerometer signal; and
  determining that the fall detection criteria are met.

2. The medical device of claim 1, wherein the control circuit is configured to determine the second body posture vector at a predetermined time interval later than the first body posture vector without verifying that the first body posture vector corresponds to an upright patient posture.

3. The medical device of claim 1, wherein:
  the telemetry circuit is further configured to receive a body posture confirmation signal from a personal device; and
  the control circuit is configured to establish the first body posture vector from the body posture signal in response to receiving the body posture confirmation signal.

4. The medical device of claim 1, wherein:
  the control circuit is further configured to determine a plurality of body posture vectors from the body posture signal over time;
  the medical device further comprises a memory configured to store each of the plurality of body posture vectors with a corresponding time and date stamp;
  the telemetry circuit is further configured to receive a data log transmitted from another device, the data log comprising a time and date stamp that is associated with a reference body posture; and
  the control circuit is configured to establish the first body posture vector by:
    identifying from the stored plurality of body posture vectors at least one body posture vector having a time and date stamp that matches the time and date stamp of the data log that is associated with the reference body posture, and
    establishing the first body posture vector based on the at least one body posture vector having the time and date stamp that matches the time and date stamp of the data log.

5. The medical device of claim 1, further comprising:
  a memory for storing fall detection data;
  wherein the control circuit is further configured to:
    determine that the fall recovery time is greater than a threshold recovery time; and
    perform a prioritized fall detection response comprising at least one of generating a fall detection alert and storing fall detection data in the memory in response to the fall recovery time being greater than the threshold recovery time.

6. The medical device of claim 1, wherein the control circuit is further configured to:
  determine a plurality of body posture vectors from the body posture signal, each one of the plurality of body posture vectors comprising at least one body posture signal component determined over a predetermined time interval;
  determine at least one directional change metric from the plurality of body posture vectors that is greater than a body posture change threshold, each one of the directional change metrics determined by determining a sum of weighted body posture signal component differences between two of the plurality of body posture vectors; and detect one of the patient fall and a fall recovery in response to at least one of the determined directional change metrics being greater than a body posture change threshold.

7. The medical device of claim 1, wherein:
the telemetry circuit is configured to receive a second truth signal indicating a missed fall detection; and
the control circuit is configured to adjust a fall detection control parameter in response to the second truth signal.

8. The medical device of claim 1, wherein:
the telemetry circuit is configured to receive a signal from a personal device indicating a communication link is established between the personal device and an appliance; and
the control circuit is configured to disable fall detection in response to the signal from the personal device.

9. The medical device of claim 1, wherein:
the accelerometer circuit is configured to generate a patient physical activity signal;
the control circuit is configured to adjust the fall detection control parameter by:
determining a patient physical activity metric from the patient physical activity signal;
determining that the patient physical activity metric is greater than a threshold activity level;
determining at least one of a directional change in a body posture vector from the body posture signal and a feature of the body acceleration signal corresponding to the patient physical activity metric; and
setting the fall detection control parameter based on one of the directional change in the body posture vector and the feature of the body acceleration signal corresponding to the patient physical activity metric.

10. The medical device of claim 1, wherein the control circuit is configured to determine that the body posture signal meets the fall detection criteria by:
determining a first directional change metric from the body posture signal during a first portion of a twenty four hour period;
switching from determining the first directional change metric to determining a second directional change metric from the body posture signal during a second portion of the twenty four hour period, wherein the second directional change metric is determined differently than the first directional change metric and corresponds to a change from a first non-upright position to a second non-upright position; and
determining that the body posture signal meets the fall detection criteria in response to one of the first directional change metric meeting a first directional change threshold and the second directional change metric meeting a second directional change threshold different than the first directional change threshold.

11. The medical device of claim 1, wherein:
the accelerometer circuit is further configured to generate a patient physical activity signal from the accelerometer signal;
the control circuit is further configured to:
determine a morphology of the patient physical activity signal in response to the body posture signal and the body acceleration signal meeting the fall detection criteria; and
withhold a patient fall detection based on the morphology of the patient physical activity signal.

12. A method for detecting a patient fall by a medical device, comprising:
producing an accelerometer signal;
generating a body posture signal and a body acceleration signal from the accelerometer signal;
determining that the body posture signal and the body acceleration signal meet fall detection criteria by:
determining a first body posture vector from the body posture signal at a first time point;
determining a second body posture vector from the body posture signal at a second time point later than the first time point of the first body posture vector;
determining a directional change metric correlated to an angle between the first body posture vector and the second body posture vector;
determining that the directional change metric is greater than a threshold directional change;
detecting an acceleration signal spike from the body acceleration signal; and
determining that the acceleration signal spike and the second time point are within a fall time window of each other;
detecting a patient fall in response to the body posture signal and the body acceleration signal meeting the fall detection criteria;
determining a third body posture vector at a third time point after the second time point;
determining a directional change metric between the third body posture vector and at least one of the first body posture vector and the second body posture vector;
determining that the directional change metric meets fall recovery criteria;
determining a fall recovery time as a time interval from the second time point to the third time point in response to the directional change metric meeting the fall recovery criteria;
determining at least one of a trend in a frequency of fall detections and a trend in fall recovery time durations in response to detecting the patient fall;
transmitting the determined trend;
receiving a first truth signal transmitted from another device indicating that the detected patient fall is a falsely detected patient fall; and
responsive to receiving the first truth signal, adjusting at least one fall detection control parameter used to control at least one of: generating the body posture signal from the accelerometer signal; generating the body acceleration signal from the accelerometer signal; and
determining that the fall detection criteria are met.

13. The method of claim 12, wherein determining the first body posture vector and the second body posture vector comprises determining the second body posture vector at a predetermined time interval later than the first body posture vector without verifying that the first body posture vector corresponds to an upright patient posture.

14. The method of claim 12, further comprising:
receiving a body posture confirmation signal from a personal device; and
establishing the first body posture vector from the body posture signal in response to receiving the body posture confirmation signal.

15. The method of claim 12, further comprising:
determining a plurality of body posture vectors from the body posture signal over time; storing each of the plurality of body posture vectors with a corresponding time and date stamp;
receiving a data log transmitted from another device, the data log comprising a time and date stamp that is associated with a reference body posture; and
establishing the first body posture vector by:
identifying from the stored plurality of body posture vectors at least one body posture vector having a time and date stamp that matches the time and date stamp of the data log that is associated with the reference body posture, and
establishing the first body posture vector based on the at least one body posture vector having a time and date stamp that matches the time and date stamp of the data log.

16. The method of claim 12, further comprising:
determining that the fall recovery time is greater than a threshold recovery time; and
performing a prioritized fall detection response comprising at least one of generating a fall detection alert and storing fall detection data in a memory in response to the fall recovery time being greater than the threshold recovery time.

17. The method of claim 12, further comprising:
determining a plurality of body posture vectors from the body posture signal, each one of the plurality of body posture vectors comprising at least one body posture signal component determined over a predetermined time interval;
determining at least one directional change metric from the plurality of body posture vectors that is greater than a body posture change threshold, each one of the directional change metrics determined by determining a sum of weighted body posture signal component differences between two of the plurality of body posture vectors; and
detecting one of the patient fall and a fall recovery in response to at least one of the determined directional change metrics being greater than a body posture change threshold.

18. The method of claim 12, further comprising:
receiving a second truth signal indicating a missed fall detection; and
adjusting a fall detection control parameter in response to the second truth signal.

19. The method of claim 12, further comprising:
receiving a signal from a personal device indicating a communication link is established between the personal device and an appliance; and
disabling fall detection in response to signal.

20. The method of claim 12, further comprising generating a patient physical activity signal from the accelerometer signal;
wherein adjusting the fall detection control parameter comprises:
determining a patient physical activity metric from the patient physical activity signal;
determining that the patient physical activity metric is greater than a threshold activity level;
determining at least one of a directional change in a body posture vector from the body posture signal and a feature of the body acceleration signal corresponding to the patient physical activity metric; and
setting the fall detection control parameter based on one of the directional change in the body posture vector or the feature of the body acceleration signal corresponding to the patient physical activity metric.

21. The method of claim 12, wherein determining that the body posture signal meets the fall detection criteria comprises:
determining a first directional change metric from the body posture signal during a first portion of a twenty four hour period;
switching from determining the first directional change metric to determining a second directional change metric from the body posture signal during a second portion of the twenty four hour period, wherein the second directional change metric is determined differently than the first directional change metric and corresponds to a change from a first non-upright position to a second non-upright position; and
determining that the body posture signal meets the fall detection criteria in response to one of the first directional change metric meeting a first directional change threshold and the second directional change metric meeting a second directional change threshold different than the first directional change threshold.

22. The method of claim 12, further comprising:
generating a patient physical activity signal from the accelerometer signal;
determining a morphology of the patient physical activity signal in response to the body posture signal and the body acceleration signal meeting the fall detection criteria; and
withholding a patient fall detection based on the morphology of the patient physical activity signal.

23. A non-transitory computer readable medium storing instructions which, when executed by a control circuit of a medical device, cause the medical device to:
produce an accelerometer signal;
generate a body posture signal and a body acceleration signal from the accelerometer signal;
determine that the body posture signal and the body acceleration signal meet fall detection criteria by:
determining a first body posture vector from the body posture signal at a first time point;
determining a second body posture vector from the body posture signal at a second time point later than the first time point of the first body posture vector;
determining a directional change metric correlated to an angle between the first body posture vector and the second body posture vector;
determining that the directional change metric is greater than a threshold directional change;
detecting an acceleration signal spike from the body acceleration signal; and
determining that the acceleration signal spike and the second time point are within a fall time window of each other;
detect a patient fall in response to the body posture signal and the body acceleration signal meeting the fall detection criteria;
determine a third body posture vector at a third time point after the second time point;
determine a directional change metric between the third body posture vector and at least one of the first body posture vector and the second body posture vector;
determine that the directional change metric meets fall recovery criteria;

determine a fall recovery time as a time interval from the second time point to the third time point in response to the directional change metric meeting the fall recovery criteria;

determine at least one of a trend in a frequency of fall detections and a trend in fall recovery time durations in response to detecting the patient fall;

transmit the determined trend;

receive a truth signal from another device that is not the medical device indicating that the detected patient fall is a falsely detected patient fall; and responsive to receiving the truth signal, adjust at least one fall detection control parameter used by the medical device to control at least one of: generating the body posture signal from the accelerometer signal; generating the body acceleration signal from the accelerometer signal; and determining that the fall detection criteria are met.

* * * * *